United States Patent
Seow et al.

(10) Patent No.: US 12,268,386 B2
(45) Date of Patent: Apr. 8, 2025

(54) DISPLACEABLE ADJUNCT ATTACHMENT FEATURES FOR SURGICAL STAPLER

(71) Applicant: Cilag GmbH International, Zug (CH)

(72) Inventors: Christopher Q. Seow, Cincinnati, OH (US); Taylor W. Aronhalt, Loveland, OH (US); Austin J. Bridges, Huntington Beach, CA (US); Zhifan Huang, Mason, OH (US)

(73) Assignee: Cilag GmbH International, Zug (CH)

( * ) Notice: Subject to any disclaimer, the term of this patent is extended or adjusted under 35 U.S.C. 154(b) by 5 days.

(21) Appl. No.: 17/514,073

(22) Filed: Oct. 29, 2021

(65) Prior Publication Data

US 2023/0139479 A1 May 4, 2023

(51) Int. Cl.
*A61B 17/068* (2006.01)
*A61B 17/072* (2006.01)

(52) U.S. Cl.
CPC ........ *A61B 17/0686* (2013.01); *A61B 17/072* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC .......... A61B 17/07292; A61B 17/0686; A61B 17/072; A61B 2017/07257; A61B 2017/07271; A61B 2017/07278; A61B 2017/07285; A61B 2017/0406; A61B 2017/2825; A61B 2017/2829; A61B 2017/0053; A61B 90/03; A61B 2090/033
USPC ............ 227/175.1–181.1; 606/148, 151, 154
See application file for complete search history.

(56) References Cited

U.S. PATENT DOCUMENTS

| | | |
|---|---|---|
| 5,711,960 A | 1/1998 | Shikinami |
| 7,147,138 B2 | 12/2006 | Shelton, IV |
| 7,380,696 B2 | 6/2008 | Shelton, IV et al. |
| 7,665,646 B2 | 2/2010 | Prommersberger |
| 8,028,883 B2 | 10/2011 | Stopek |
| 8,210,411 B2 | 7/2012 | Yates et al. |

(Continued)

FOREIGN PATENT DOCUMENTS

| | | |
|---|---|---|
| EP | 3150143 A1 | 4/2017 |
| EP | 3791806 A1 | 3/2021 |

OTHER PUBLICATIONS

European Examination Report dated Sep. 14, 2023 for Application No. EP 22797890.5, 3 pgs.

(Continued)

*Primary Examiner* — Stephen F. Gerrity
*Assistant Examiner* — Linda J Hodge
(74) *Attorney, Agent, or Firm* — Frost Brown Todd LLP

(57) ABSTRACT

An apparatus includes an adjunct body and a plurality of movable members. The adjunct body defines an adjunct surface for contacting a tissue, and the adjunct body is configured to overlie and directly contact a deck of a surgical stapler. The plurality of movable members are coupled with the adjunct body, and each movable member of the plurality of movable members is individually operable to move from a first configuration to a second configuration in response to a firing operation of a surgical stapler. The movable members in the first configuration are configured to couple the adjunct body with the deck, and the movable members in the second configuration are configured to enable the adjunct body to separate from the deck.

20 Claims, 24 Drawing Sheets

(56) References Cited

U.S. PATENT DOCUMENTS

| | | |
|---|---|---|
| 8,348,130 B2 | 1/2013 | Shah et al. |
| 8,371,491 B2 | 2/2013 | Huitema et al. |
| 8,408,439 B2 | 4/2013 | Huang et al. |
| 8,453,652 B2 | 6/2013 | Stopek |
| 8,453,914 B2 | 6/2013 | Laurent et al. |
| 8,479,968 B2 | 7/2013 | Hodgkinson et al. |
| 8,757,465 B2 | 6/2014 | Woodard, Jr. et al. |
| 8,893,949 B2 | 11/2014 | Shelton, IV et al. |
| 8,967,448 B2 | 3/2015 | Carter et al. |
| 9,055,941 B2 | 6/2015 | Schmid et al. |
| 9,186,142 B2 | 11/2015 | Fanelli et al. |
| 9,232,941 B2 | 1/2016 | Mandakolathur Vasudevan et al. |
| 9,289,207 B2 | 3/2016 | Shelton, IV |
| 9,301,752 B2 | 4/2016 | Mandakolathur Vasudevan et al. |
| 9,301,753 B2 | 4/2016 | Aldridge et al. |
| 9,307,989 B2 | 4/2016 | Shelton, IV et al. |
| 9,314,246 B2 | 4/2016 | Shelton, IV et al. |
| 9,332,974 B2 | 5/2016 | Henderson et al. |
| 9,364,233 B2 | 6/2016 | Alexander, III et al. |
| 9,480,476 B2 | 11/2016 | Aldridge et al. |
| 9,517,065 B2 | 12/2016 | Simms et al. |
| 9,585,657 B2 | 3/2017 | Shelton, IV et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,918,716 B2 | 3/2018 | Baxter, III et al. |
| 9,936,950 B2 | 4/2018 | Shelton, IV et al. |
| 10,092,292 B2 | 10/2018 | Boudreaux et al. |
| 10,166,023 B2 | 1/2019 | Vendely et al. |
| 10,172,620 B2 | 1/2019 | Harris et al. |
| 10,258,330 B2 | 4/2019 | Shelton, IV et al. |
| 10,285,691 B2 | 5/2019 | Shelton, IV et al. |
| 10,285,699 B2 | 5/2019 | Vendely et al. |
| 10,293,553 B2 | 5/2019 | Racenet et al. |
| 10,307,160 B2 | 6/2019 | Vendely et al. |
| 10,327,776 B2 | 6/2019 | Harris et al. |
| 10,327,777 B2 | 6/2019 | Harris et al. |
| 10,342,542 B2 | 7/2019 | Barton et al. |
| 10,349,939 B2 | 7/2019 | Shelton, IV et al. |
| 10,357,251 B2 | 7/2019 | Shelton, IV et al. |
| 10,433,846 B2 | 10/2019 | Vendely et al. |
| 10,441,285 B2 | 10/2019 | Shelton, IV et al. |
| 10,485,544 B2 | 11/2019 | Shelton, IV et al. |
| 10,524,788 B2 | 1/2020 | Vendely et al. |
| 10,548,597 B2 | 2/2020 | Dunki-Jacobs et al. |
| 10,568,621 B2 | 2/2020 | Shelton, IV et al. |
| 10,569,071 B2 | 2/2020 | Harris et al. |
| 10,588,623 B2 | 3/2020 | Schmid et al. |
| 10,624,861 B2 | 4/2020 | Widenhouse et al. |
| 10,667,808 B2 | 6/2020 | Baxter, III et al. |
| 10,709,452 B2 | 7/2020 | DiNardo et al. |
| 10,765,426 B2 | 9/2020 | Shelton, IV et al. |
| 10,856,866 B2 | 12/2020 | Shelton, IV et al. |
| 10,869,663 B2 | 12/2020 | Shelton, IV et al. |
| 10,945,731 B2 | 3/2021 | Baxter, III et al. |
| 10,966,722 B2 | 4/2021 | Shelton, IV et al. |
| 10,980,539 B2 | 4/2021 | Harris et al. |
| 10,987,102 B2 | 4/2021 | Gonzalez et al. |
| 11,033,266 B2 | 6/2021 | Jones et al. |
| 11,058,425 B2 | 7/2021 | Widenhouse et al. |
| 11,202,633 B2 | 12/2021 | Harris et al. |
| 11,219,451 B2 | 1/2022 | Shelton, IV et al. |
| 11,432,815 B2 | 9/2022 | Courtwright et al. |
| 11,504,115 B2 | 11/2022 | Shelton, IV et al. |
| 11,660,093 B2 | 5/2023 | Bakos et al. |
| 11,672,538 B2 | 6/2023 | Baril et al. |
| 2006/0173470 A1 | 8/2006 | Oray et al. |
| 2008/0314960 A1* | 12/2008 | Marczyk .............. A61B 17/105 606/220 |
| 2012/0080336 A1 | 4/2012 | Shelton, IV et al. |
| 2012/0083836 A1* | 4/2012 | Shelton, IV ......... A61B 17/072 206/339 |
| 2013/0082086 A1* | 4/2013 | Hueil ................. A61B 17/0644 227/177.1 |
| 2013/0146642 A1* | 6/2013 | Shelton, IV ...... A61B 17/07207 227/177.1 |
| 2013/0256373 A1* | 10/2013 | Schmid ............ A61B 17/07207 227/176.1 |
| 2014/0224686 A1* | 8/2014 | Aronhalt ............ A61B 17/0644 206/339 |
| 2014/0224857 A1 | 8/2014 | Schmid |
| 2015/0196296 A1* | 7/2015 | Swayze ............ A61B 17/07207 227/176.1 |
| 2018/0235615 A1* | 8/2018 | Landgrebe ........... A61B 17/072 |
| 2020/0214706 A1 | 7/2020 | Vendely et al. |
| 2021/0077094 A1 | 3/2021 | Harris et al. |
| 2022/0079579 A1 | 3/2022 | Shelton, IV et al. |
| 2023/0139613 A1 | 5/2023 | Seow et al. |
| 2023/0140285 A1 | 5/2023 | Boudreaux |

OTHER PUBLICATIONS

International Search Report and Written Opinion dated Jan. 5, 2023 for Application No. PCT/IB2022/060268, 13 pgs.
International Search Report and Written Opinion dated Jan. 5, 2023 for Application No. PCT/IB2022/060272, 15 pgs.
International Search Report and Written Opinion dated Jan. 5, 2023 for Application No. PCT/IB2022/060274, 16 pgs.
European Extended Search Report and Written Opinion dated Apr. 19, 2024, for Application No. 24164637.1, 11 pages.
U.S. Appl. No. 18/586,700, entitled "Discrete Adjunct Attachment Features for Surgical Stapler," filed Feb. 26, 2024.
U.S. Pat. No. 11,950,781 Apr. 9, 2024 Seow et al.
U.S. Pat. No. 11,998,204; and Jun. 4, 2024 Boudreaux.

* cited by examiner

DISPLACEABLE ADJUNCT ATTACHMENT FEATURES FOR SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
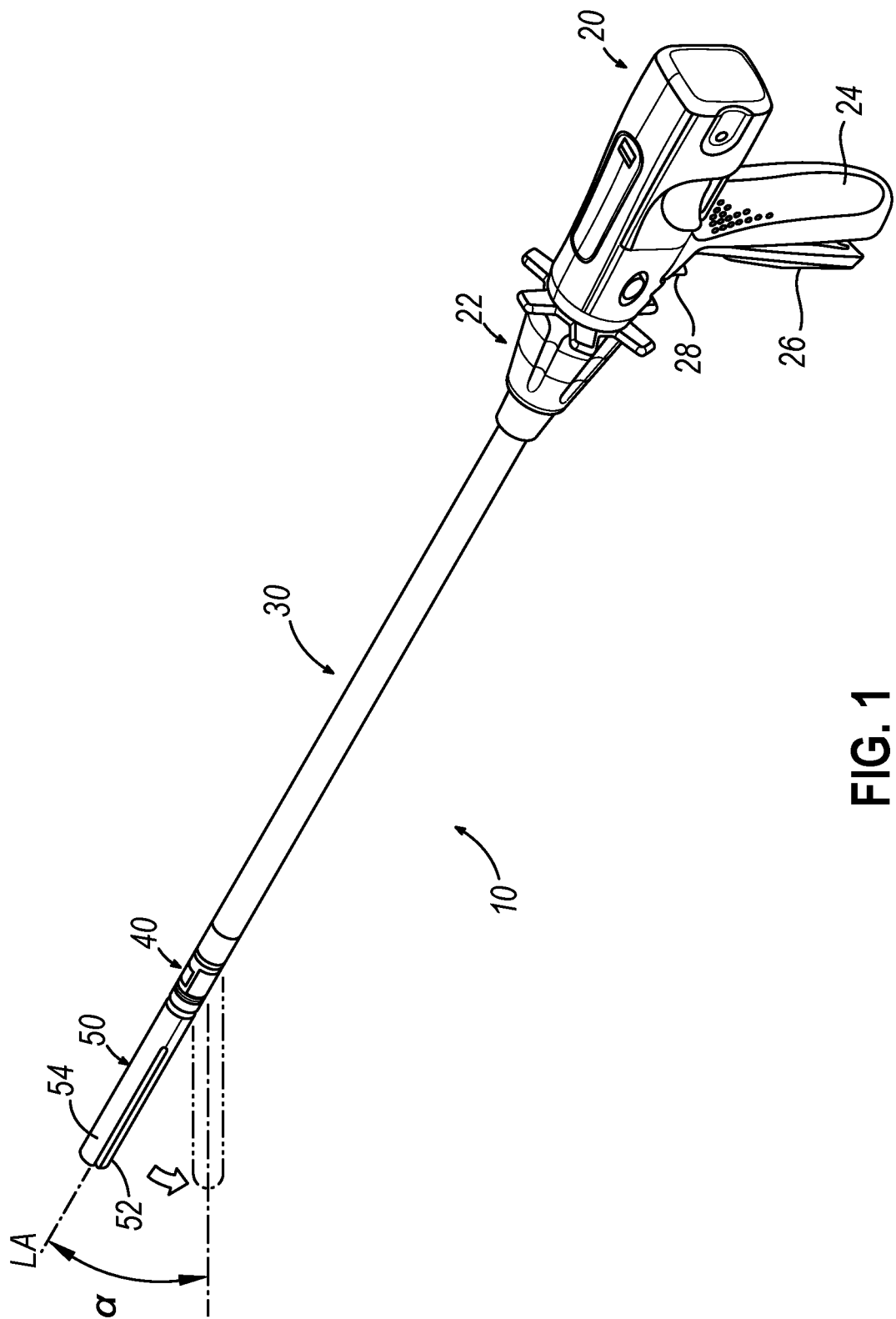
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. EXEMPLARY SURGICAL STAPLER

Figure 2:
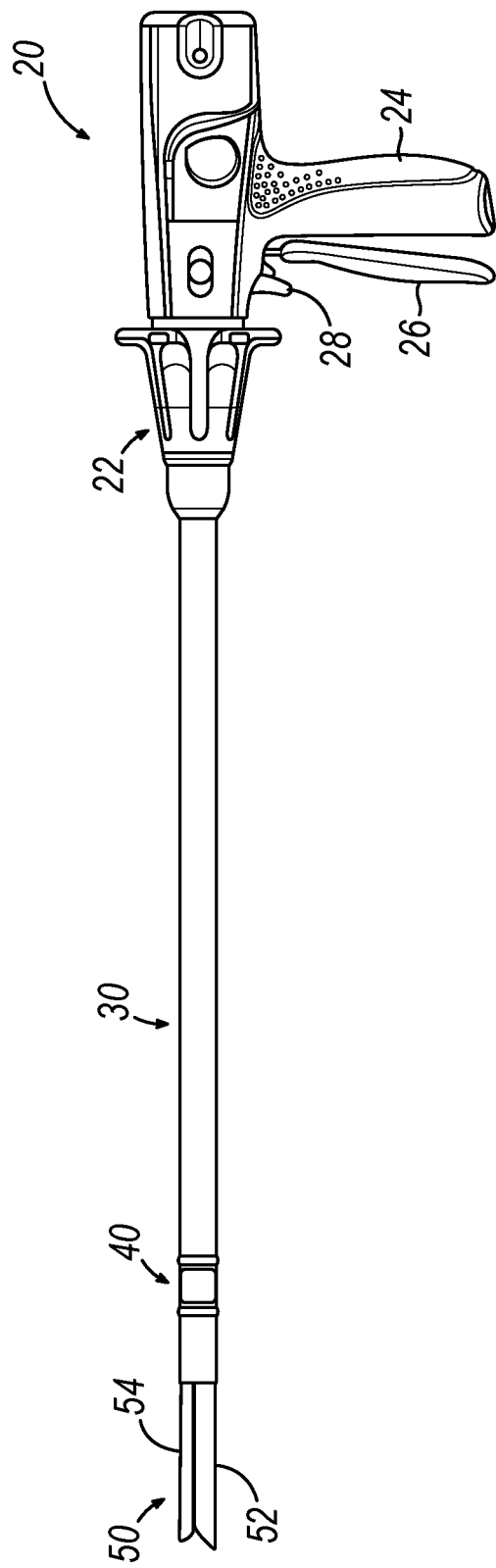
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (a) via actuation of an articulation control feature (22) of handle assembly (20).

Figure 3:
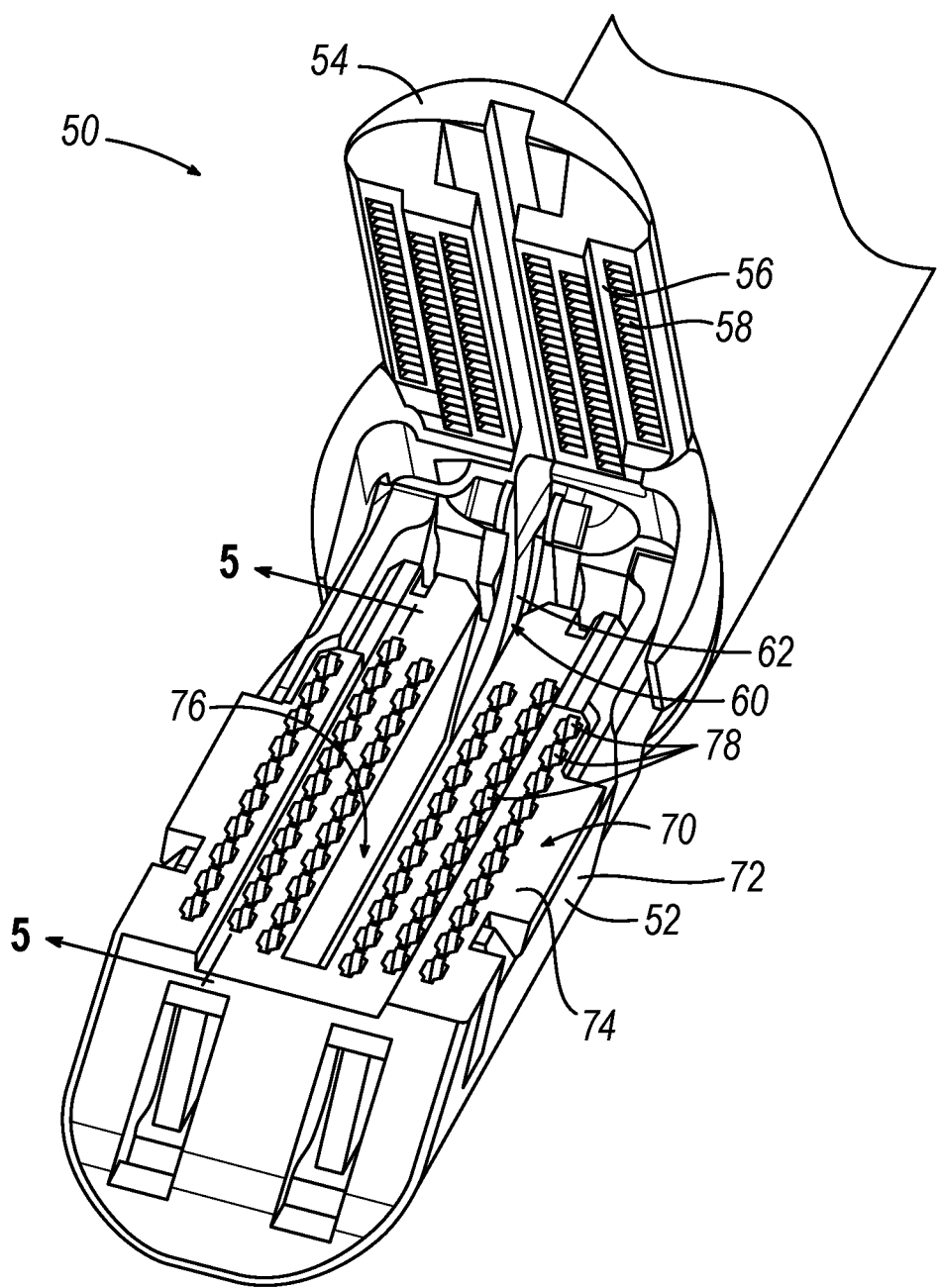
FIG. 3 depicts a perspective view of an end effector of the surgical stapler of FIG. 1 in an open state.
Figure 4:
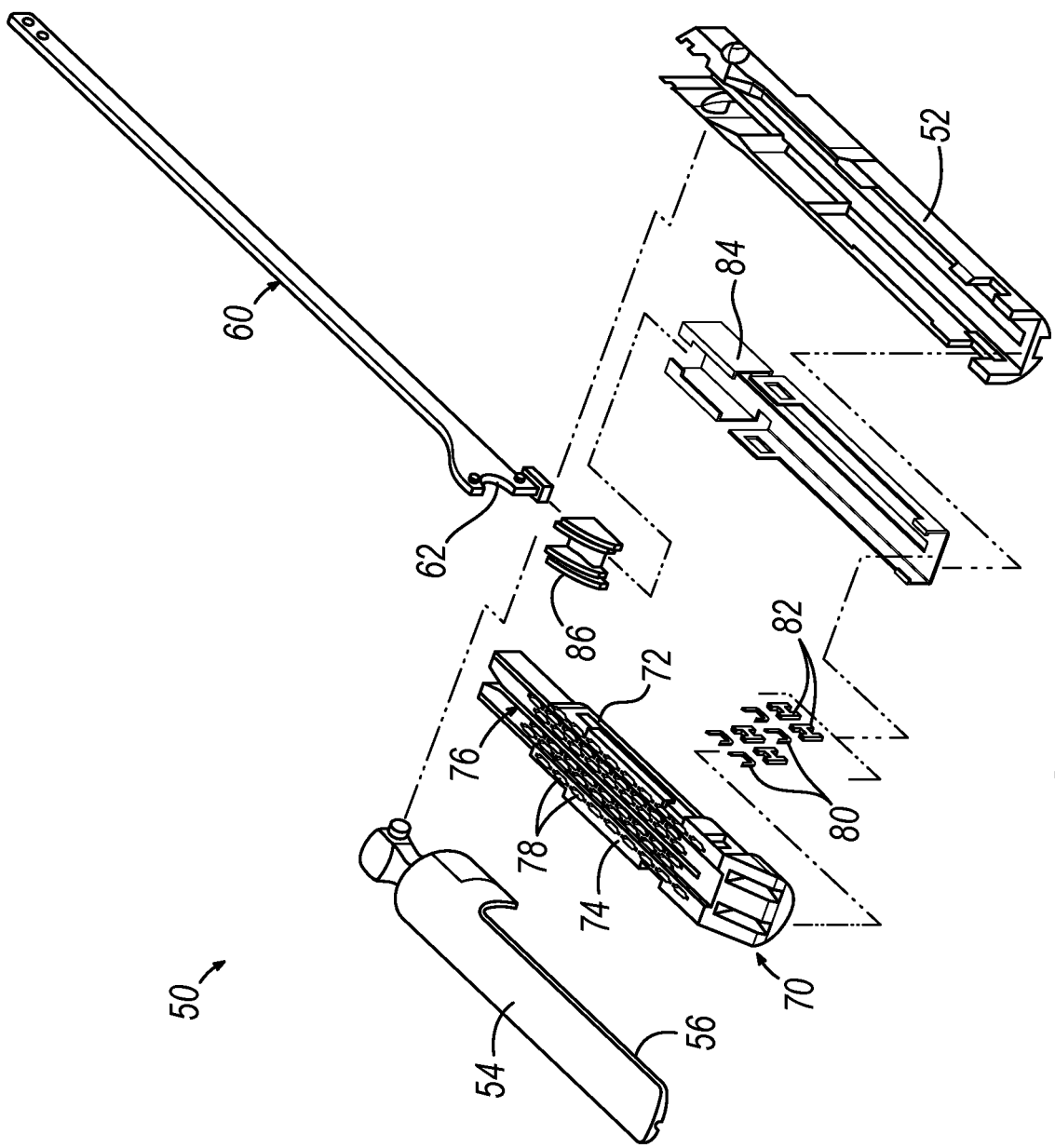
FIG. 4 depicts an exploded perspective view of the end effector of FIG. 3.

As shown best in FIGS. 3 and 4, end effector (50) includes a lower jaw (52) that supports a stapling assembly in the form of a replaceable staple cartridge (70), and an upper jaw (54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate jaw (54) toward lower jaw (16) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
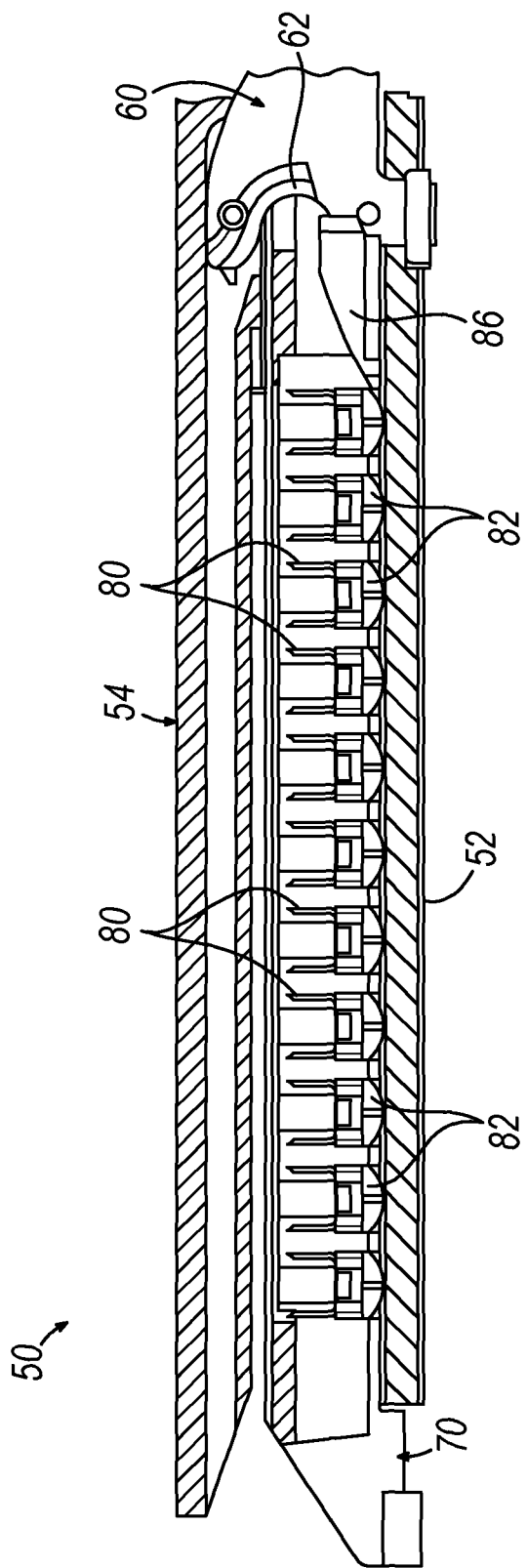
FIG. 5A depicts a side cross-sectional view of the end effector of FIG. 3, taken along line 5-5 of FIG. 3, with a firing member in a proximal position.
Figure 5B:
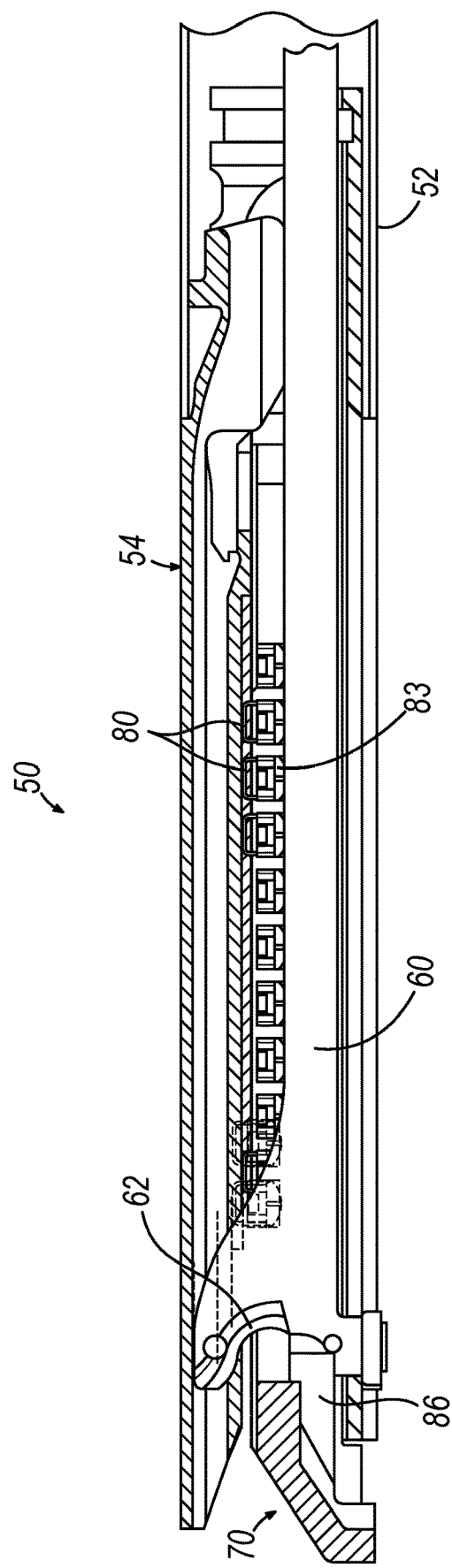
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
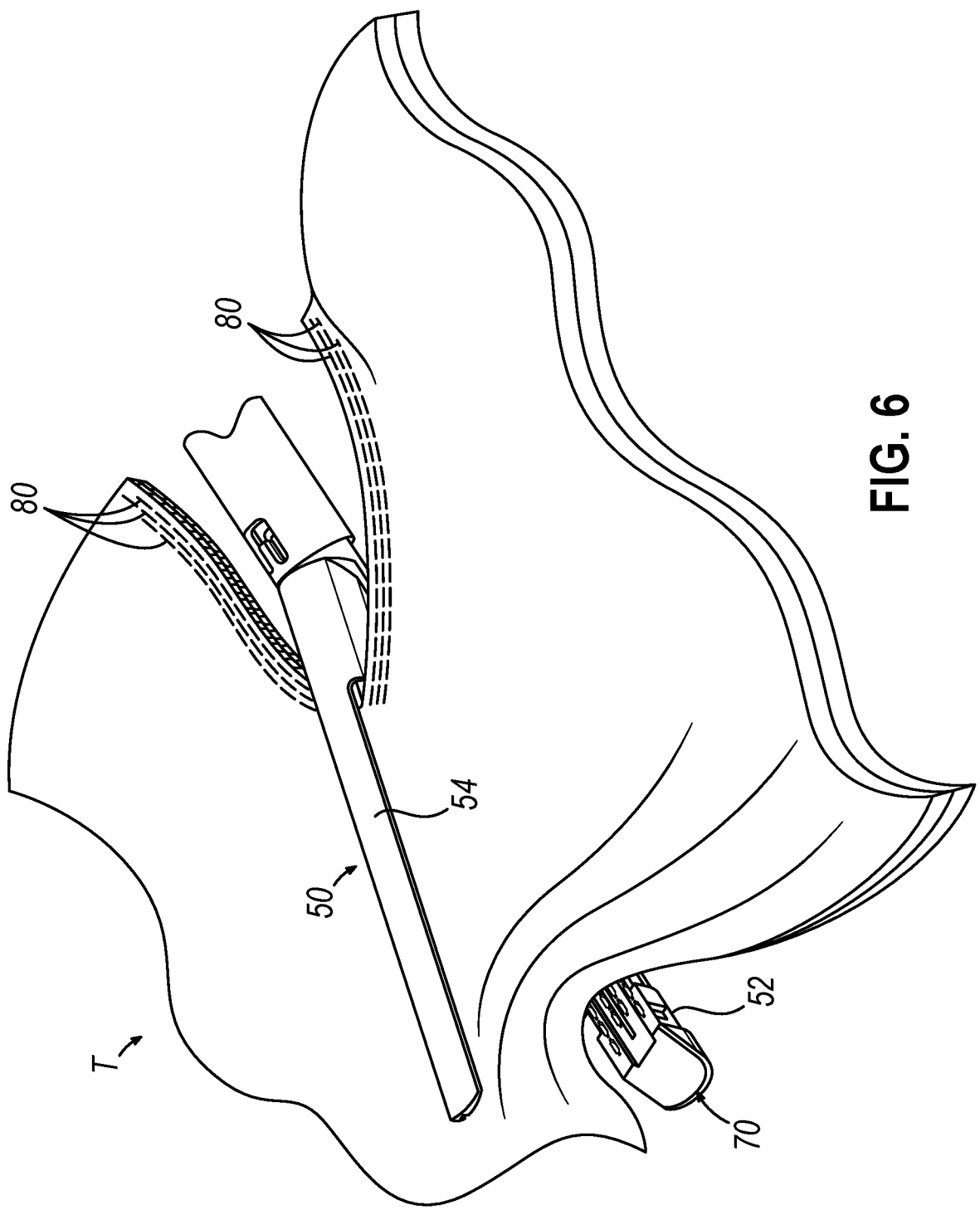
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. EXEMPLARY BUTTRESS ASSEMBLY

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
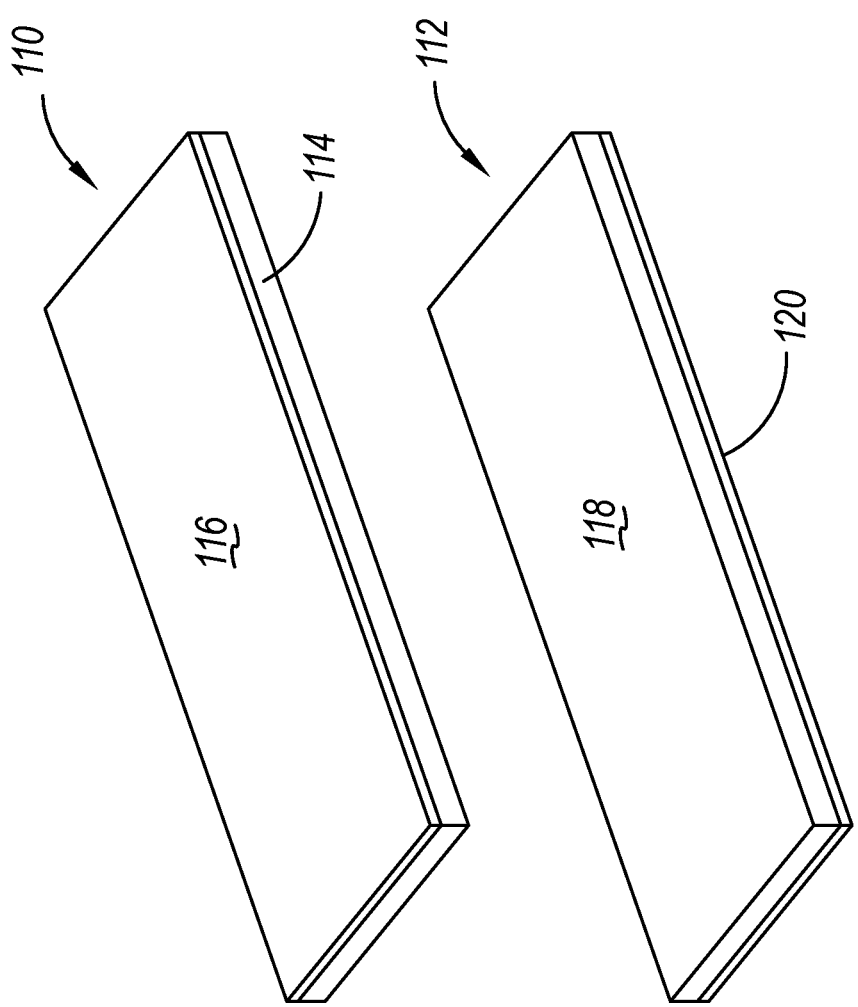
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

Figure 8A:
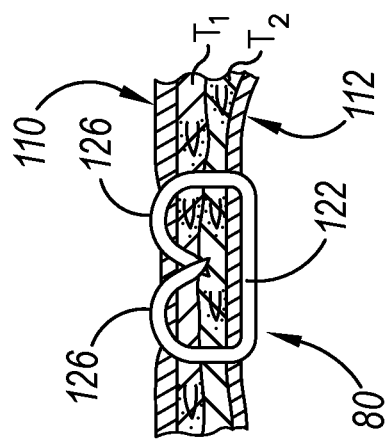
FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws.
Figure 8B:
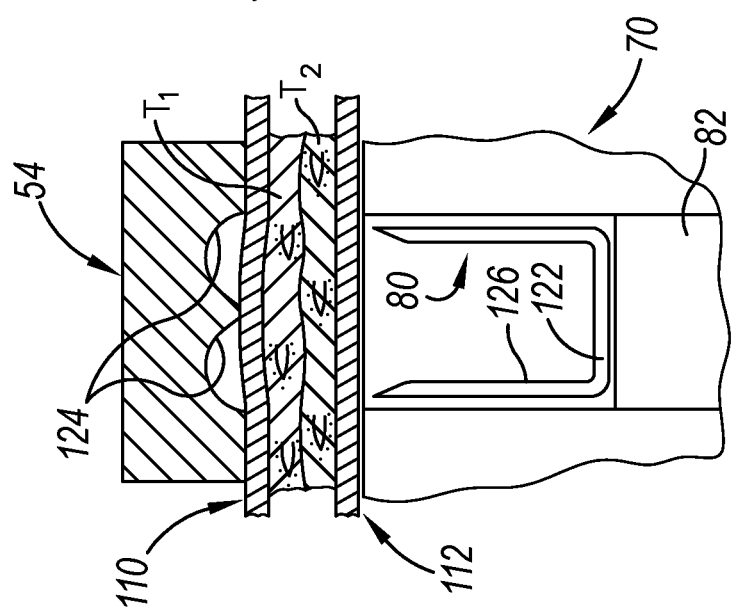
FIG. 8B depicts a cross-sectional end view of the end effector and buttress assemblies of FIG. 8A, showing the end effector jaws in a closed state on the tissue.
Figure 8C:
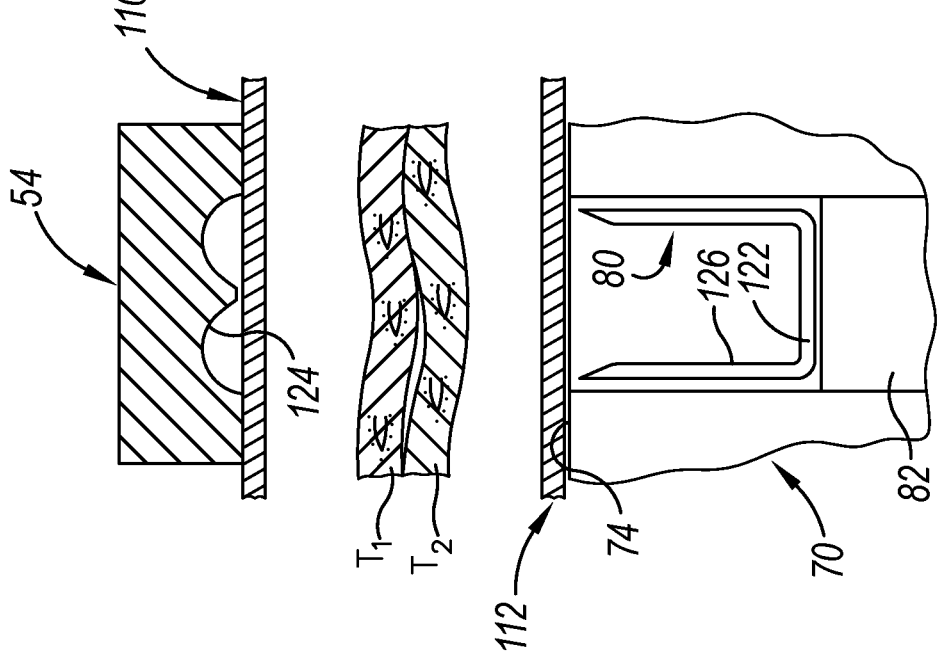
FIG. 8C depicts a cross-sectional view of a formed staple and the buttress assemblies of FIG. 8A after having been secured to the tissue by the end effector of FIG. 3.

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
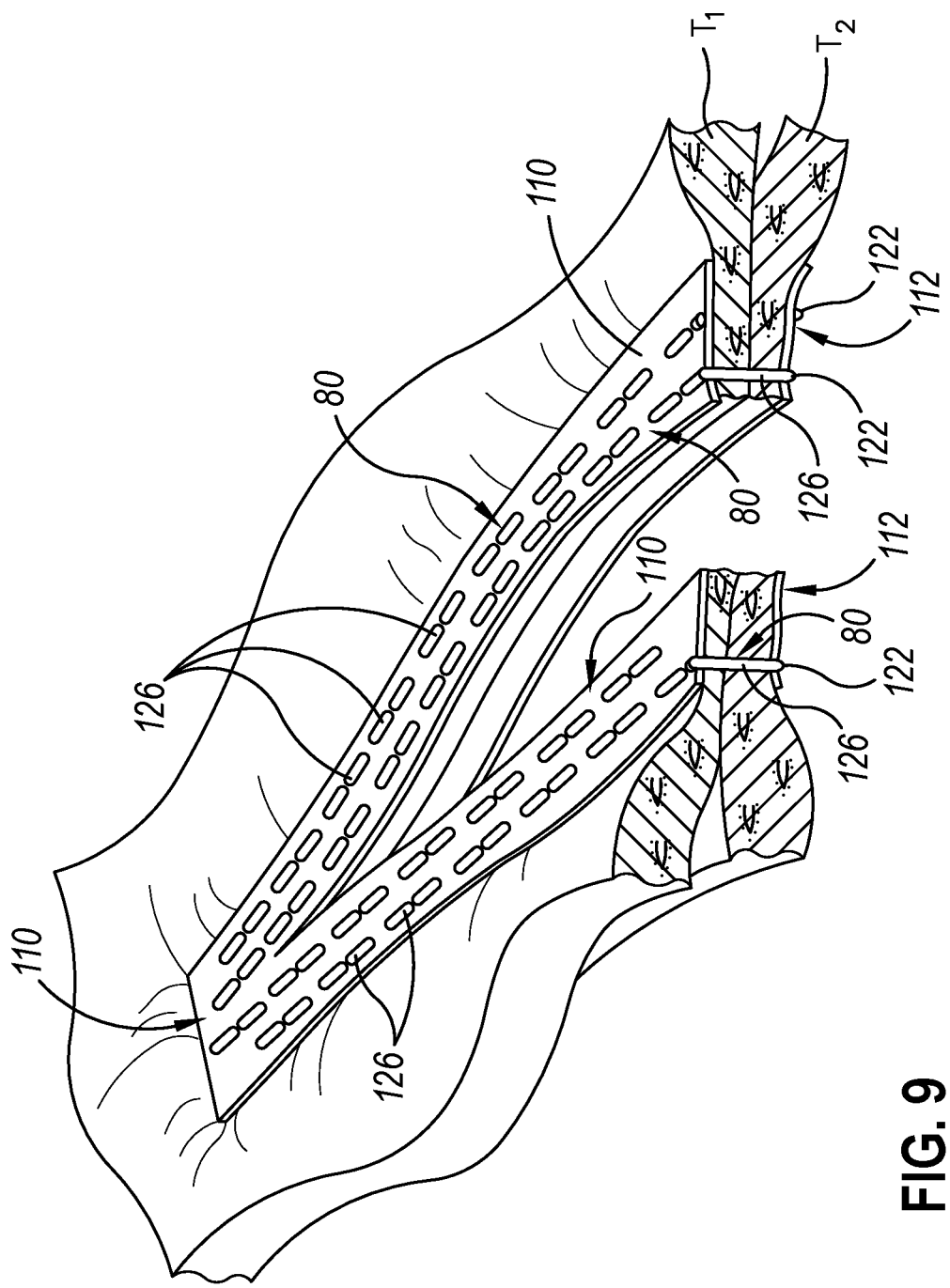
FIG. 9 depicts a perspective view of formed staples and the buttress assemblies of FIG. 8A after having been secured to the tissue by the end effector of FIG. 3.
Figure 10:
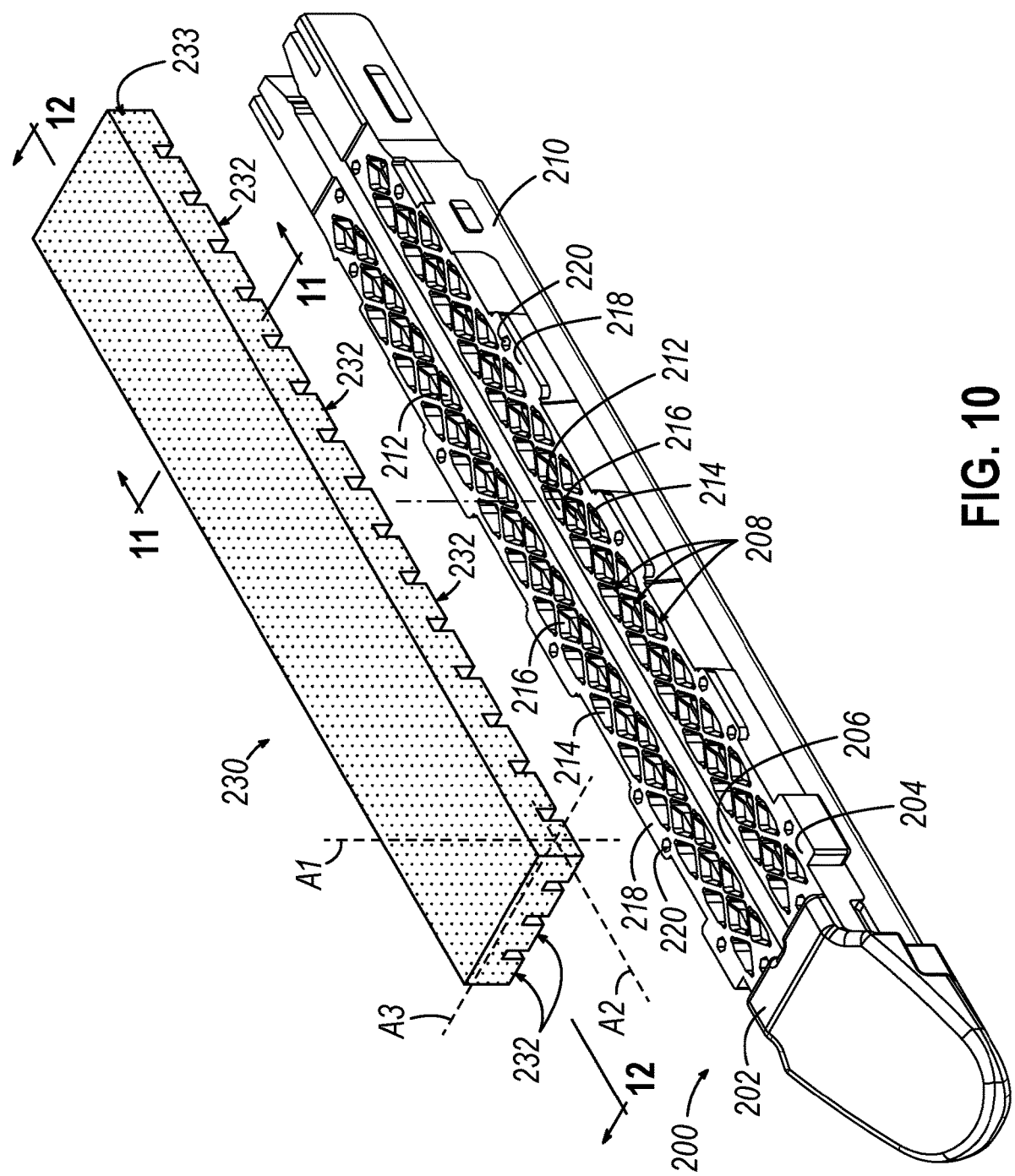
FIG. 10 depicts a perspective view of another exemplary staple cartridge in combination with a first alternative exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, issued as U.S. Pat. No. 11,660,093 on May 30, 2023, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. EXEMPLARY COMPRESSIBLE ADJUNCT

Figure 11:
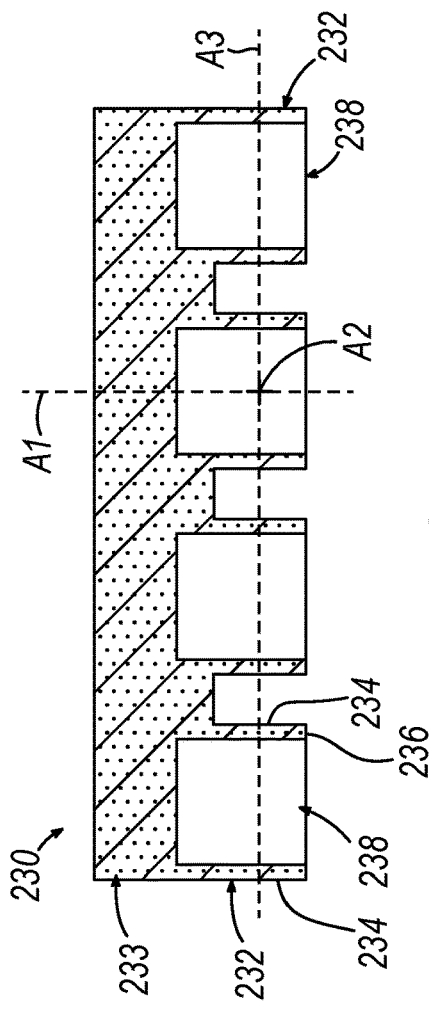
FIG. 11 depicts a cross-sectional view of the adjunct of FIG. 10, taken along line 11-11 of FIG. 10.
Figure 12:
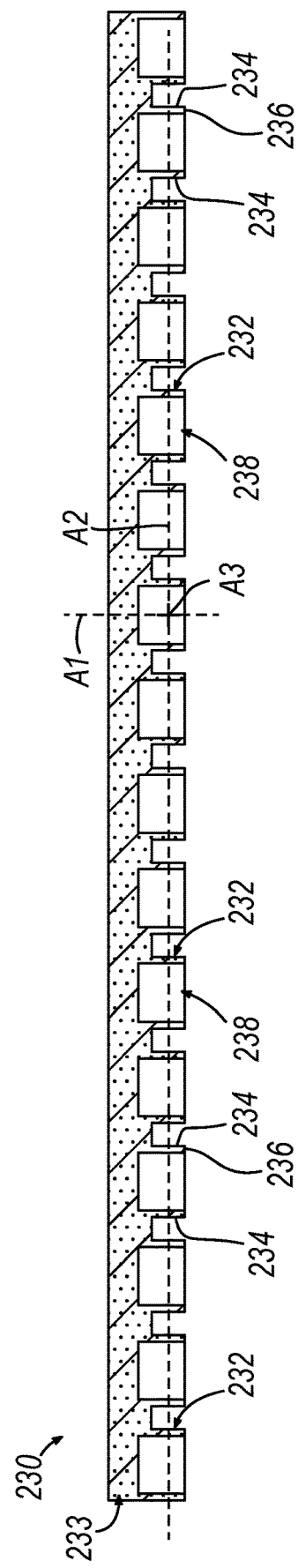
FIG. 12 depicts a cross-sectional view of the adjunct of FIG. 10, taken along line 12-12 of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape. In the present example, adjunct (230) includes four axial rows of nodules (232) each extending in a proximal-distal direction to define a length of adjunct (230), and sixteen transverse rows of nodules (232) each extending in a direction transverse to a length of staple cartridge (200) to define a transverse width of adjunct (230). It will be appreciated that adjunct (230) of other versions may have various other quantities and configurations of nodules (232).

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid. It will be appreciated that nodules (232) may be alternatively shaped in other versions of adjunct (230). Though not shown, in some versions one or more of side surfaces (234) of each nodule (232) may include an opening that communicates with the hollow interior of the nodule (232). Additionally, in some versions, adjacent nodules (232) may be interconnected at side surfaces (234) by connecting structures, which may define respective lumens between the hollow interiors of adjacent nodules (232).

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3). Additionally, adjunct (230) may be formed as a monolithic structure via an additive manufacturing process, for example. It will be appreciated that adjunct (230) may be further or alternatively constructed and operable in accordance with any of the other teachings made herein, and/or with the teachings of any of the patent references incorporated by reference here.

Adjunct (230) may be releasably attached to a deck of a staple cartridge, such as decks (74, 204) of staple cartridges (70, 200), via one or more attachment features, examples of which are described in greater detail below. It will be appreciated that adjunct (230) may be attached to a staple cartridge with or without an applicator device.

IV. EXEMPLARY FEATURES FOR ATTACHING ADJUNCT TO STAPLE CARTRIDGE

In some instances, it may be desirable to provide an adjunct with one or more features for releasably and mechanically attaching the adjunct to the deck of a staple cartridge, such as either of staple cartridges (70, 200) described above. Exemplary versions of such adjunct attachment features are described in greater detail below. Unless otherwise described, it will be appreciated that such attachment features may be applied to a multi-layer adjunct similar to buttress assemblies (110, 112) described above in connection with FIGS. 7-9, or alternatively to a compressible monolithic adjunct similar to adjunct (230) described above in connection with FIGS. 10-12. As will be described, some exemplary adjunct attachment features may be configured to release the adjunct from the deck of a staple cartridge in response to firing of the staple cartridge (referred to as "active" release). Other exemplary adjunct attachment features may be configured to release an adjunct from the deck of a staple cartridge simply in response to separation of the surgical stapler end effector from the stapled tissue (referred to as "passive" release). Additionally, unless otherwise described, it will be appreciated that the exemplary adjunct attachment features may be constructed of a different material than a tissue-contacting body portion of the corresponding adjunct, such that the body portion comprises a first material and the adjunct attachment feature comprises a second material.

A. Exemplary Adjunct with Knife Slot Attachment Features

Figure 13:
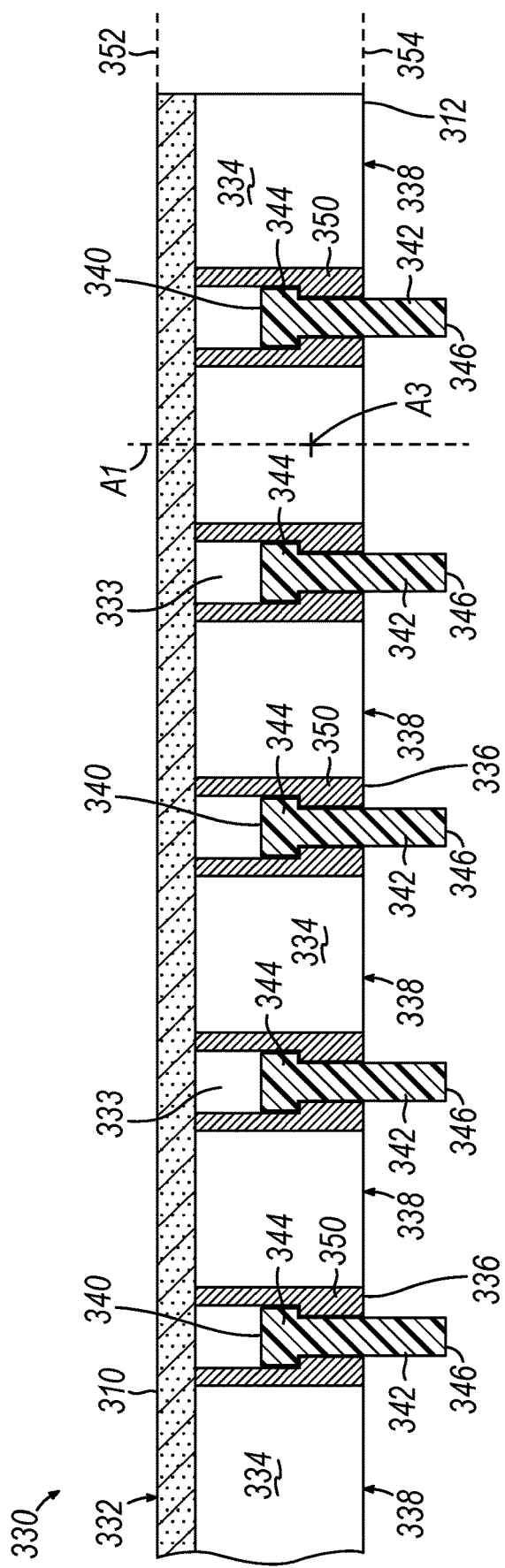
FIG. 13 depicts a cross-sectional view taken along a longitudinal centerline of a second alternative exemplary adjunct configured for use with the staple cartridge of FIG.

FIG. 13 shows another exemplary compressible adjunct (330) configured for releasable attachment to staple cartridge (200). Adjunct (330) has a monolithic body defined by a plurality of three-dimensional, resiliently compressible nodules (332) that are integrally connected with one another in a plurality of linear arrays defining a lattice structure having an elongate rectangular shape in a manner similar to that described above in connection with FIGS. 10-12. Each nodule (332) of the present example has a generally cuboid shape defining four side surfaces (334), a lower surface (336), and an opening (338) in lower surface (336) that extends along a vertical central axis (A1) of nodule (332) and defines an open, hollow interior of nodule (332). Additionally, each nodule (332) is symmetrical about its centroid along a second axis (A2) of nodule (332) that extends horizontally in a proximal-distal direction parallel to the length of adjunct (330), and along a third axis (A3) of nodule (332) that extends horizontally in a direction traverse to the length of adjunct (330), where each axis (A1, A2, A3) extends through the centroid. It will be appreciated that nodules (332) may be alternatively shaped in other versions of adjunct (330).

In the example shown, adjunct (330) further includes one or more attachment features in the form of movable pins (340) positioned along a longitudinal centerline of adjunct (330) between adjacent side surfaces (334) of nodules (332) and configured to be at least partially received within elongate slot (206) of staple cartridge (200). Each pin (340) includes a head (344) and a generally downwardly-extending post (342) that extends away from head (344). Each pin (340) is configured to translate parallel to axis (A1) within a cavity (333) formed between adjacent side surfaces (334) separating distinct nodules (332). Head (344) of each pin (340) is shaped and sized to interact with a pin stop (350) formed within each cavity (333), each pin stop (350) being configured to prevent pin (340) from falling out of cavity (333) or otherwise to prevent post (342) from extending too far outwardly from adjunct (330) such that pins (340) are unable to operate as will be described below.

Similar to adjunct (330), pins (340) may be formed of an elastic, bioabsorbable polymeric material having a suitable degree of elasticity that enables pins (340) to compress slightly when end effector (50) is closed, and a suitable density that enables pins (340) to translate and be cut during a firing stroke as will be described below.

Each pin (340) is configured to translate within each cavity (333) such that, in the first configuration where adjunct (330) is coupled with elongate slot (206) of cartridge body (202), lower surface (346) of each post (342) extends beyond the plane (354) formed by the lower surfaces (336) of each nodule (332) and into elongate slot (206). In this first configuration, posts (342) are inserted into elongate slot (206) with an interference fit (also referred to herein as a press fit) to provide a secure yet releasable coupling between adjunct (330) and cartridge body (202). Each pin (340) is further configured to translate within each cavity (333) such that, in the second configuration where adjunct (330) is decoupled from elongate slot (206) of cartridge body (202), lower surface (346) of each post (342) moves above the plane (354) formed by the lower surfaces (336) of each nodule (332) to thereby release adjunct (330) from staple cartridge (200). In this second configuration, heads (344) do not extend beyond the upper plane (352) defined by an upper surface (310) of adjunct (330), for example as shown in FIGS. 14A-14B described below.

Figure 14A:
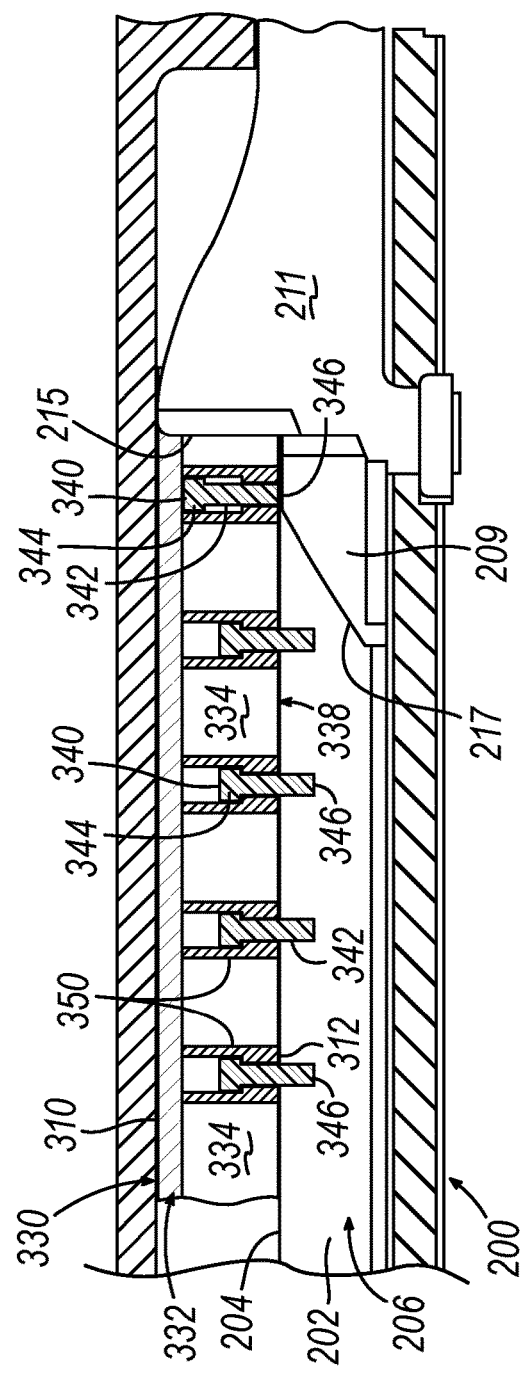
FIG. 14A depicts a cross-sectional view taken along a longitudinal centerline of the adjunct and staple cartridge of FIG. 13, shown in an early stage of a firing stroke.
Figure 14B:
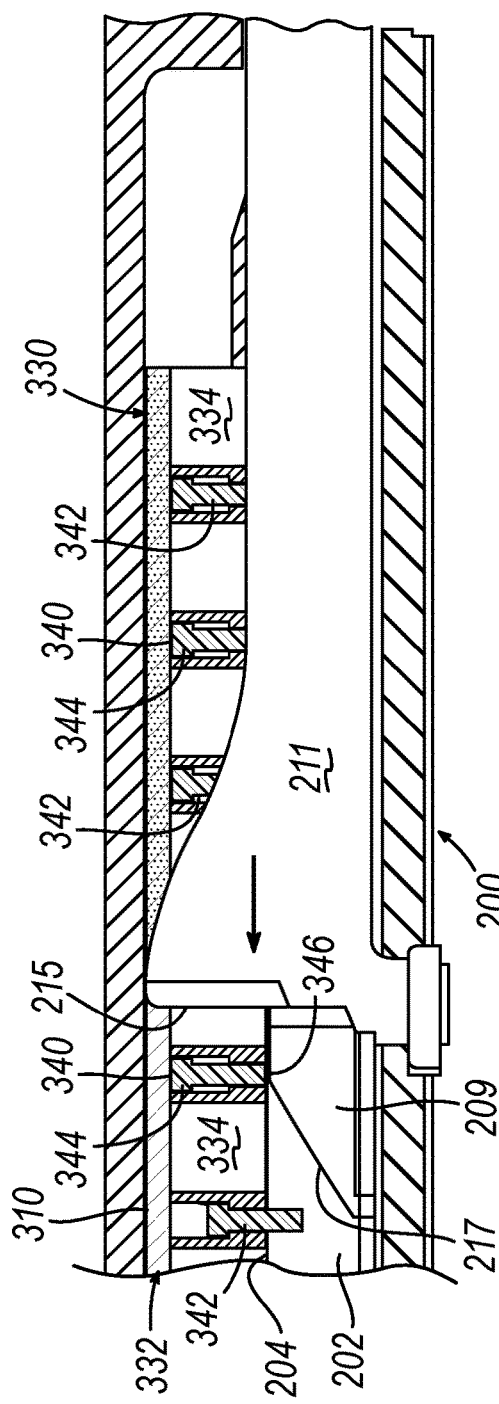
FIG. 14B depicts a cross-sectional view taken along a longitudinal centerline of the adjunct and staple cartridge of FIG. 13, shown in a later stage of a firing stroke.

With reference to FIGS. 14A and 14B, staple cartridge (200) and adjunct (330) are configured for use with end effector (50). Adjunct (330) is similar to adjunct (230) described above except as otherwise described below. Staple cartridge (200), as described above, includes a cartridge body (202) having an upwardly facing deck (204), an elongate slot (206) extending along a central axis of cartridge body (202) and opening upwardly through deck (204), and a plurality of staple openings (not shown) extending through deck (204) on each side of elongate slot (306). Each staple opening (not shown) slidably houses an unformed staple (not shown), similar to staple (80), and a respective staple driver (not shown), similar to staple driver (82), configured to drive the staple outwardly toward anvil (56) to be formed. Staple cartridge (200) further includes a wedge sled (209) similar to wedge sled (86) that it is longitudinally translatable through elongate slot (206) of cartridge body (202) by way of being operatively coupled with a firing member (211) that operates similar to firing member (60). Accordingly, during a staple firing, firing member (211) drives wedge sled (209) distally to actuate staple drivers upwardly and thereby eject staples from staple cartridge (200) into clamped tissue.

As shown in FIG. 14A, adjunct (330) may be selectively attached to staple cartridge deck (204) via pins (340) when pins (340) are in the extended state as described in the first configuration as noted above. As shown in FIG. 14B, adjunct (330) may be released from staple cartridge deck (204) by way of a leading cam surface (217) of wedge sled (209) contacting lower surface (346) of pins (340) sequentially and driving them upwardly out of elongated slot (206) of cartridge body (202). Leading cam surface (217) is defined by a central vertical rail of wedge sled (209) that translates distally through elongate slot (206) during a firing stroke. More particularly, pins (340) of the present version are configured to retract from elongated slot (206) and actively release adjunct (330) from staple cartridge deck (204) in response to firing of staple cartridge (200) during a staple firing by way of firing member (211) driving wedge sled (209), and also cutting edge (215), distally through cartridge body (202). Further, adjunct (330) may be split in half longitudinally (i.e., parallel to axis A2) during a firing stroke of surgical stapler (10). Similar to firing member (60), firing member (211) is configured to simultaneously cut tissue during a firing stroke via a distally presented cutting edge (215). Because each pin (340) is recessed upwardly within a respective cavity (333) of adjunct (330) following ejection from elongate slot (206) by the distally translating wedge sled (209), cutting edge (215) is configured to cut through pins (340) in addition to cutting through a body of adjunct (330) and tissue during a firing stroke, therefore severing adjunct (330) approximately in half longitudinally during the firing stroke.

Figure 15A:
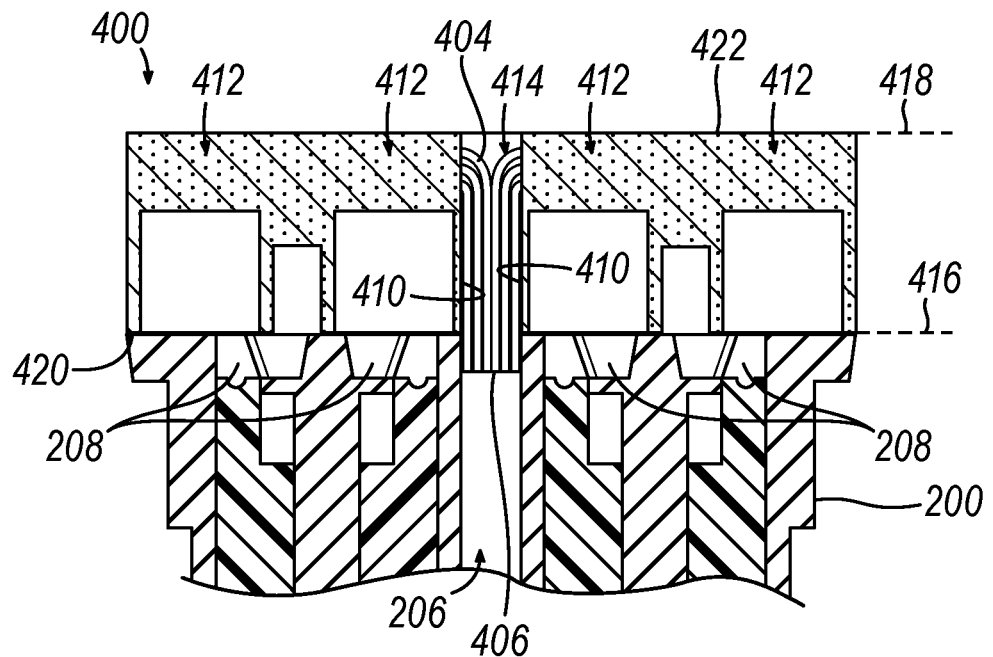
FIG. 15A depicts a cross-sectional view taken along a transverse axis of a third alternative exemplary adjunct configured for use with the staple cartridge of FIG. 10, shown in an early stage of a firing stroke.
Figure 15B:
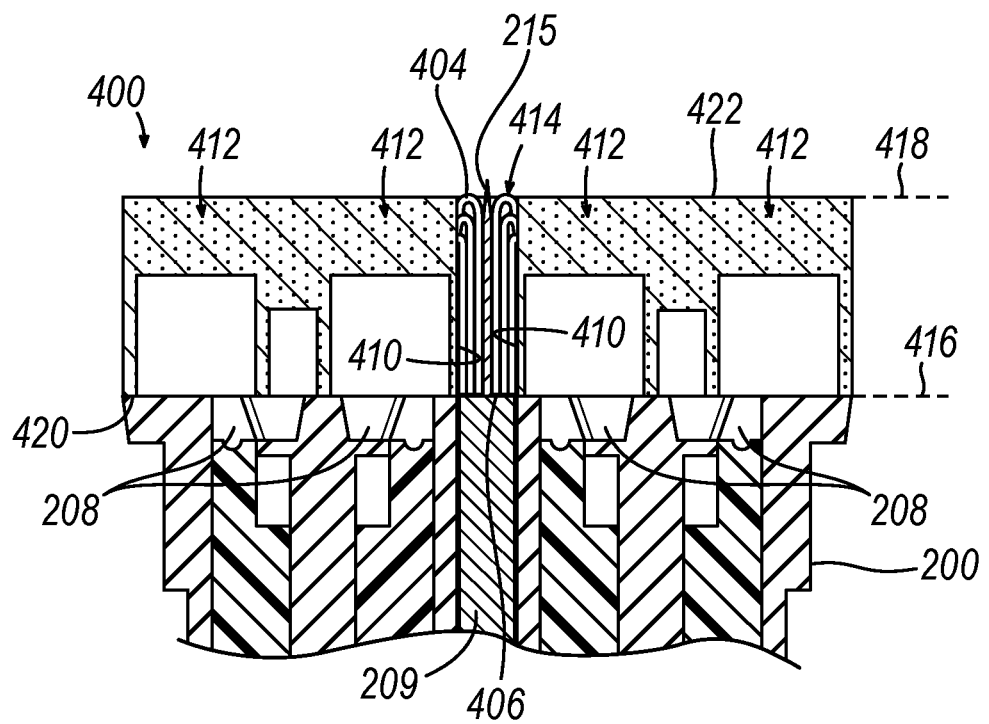
FIG. 15B depicts a cross-sectional view taken along the transverse axis of the adjunct of FIG. 15A, shown in a later stage of a firing stroke.

FIGS. 15A-15B show another exemplary compressible adjunct (400) configured for releasable attachment to staple cartridge (200). Adjunct (400) includes all of the same features as adjunct (330), except for the differences as noted below. Specifically, adjunct (400) provides an alternative to pins (340). In the example shown, adjunct (400) instead includes one or more attachment features in the form of moveable clusters of bristles (402) positioned along a longitudinal centerline of adjunct (400) between adjacent side surfaces (410) of nodules (412) and configured to be at least partially received within elongate slot (206) of staple cartridge (200). Each cluster of bristles (402) includes an upper portion (404) and a generally downwardly-extending lower portion (406) that extends away from upper portion (404). Similar to adjunct (330), for adjunct (400), each cluster of bristles (402) is configured to tightly fit within elongated slot (206) and translate parallel to axis (A1) within cavity (414) (shown occupied by bristles (402)) formed between adjacent side surfaces (410) separating distinct nodules (412).

Each bristle cluster (402) is configured to translate within each cavity (414) such that, in the first configuration where adjunct (400) is coupled with elongate slot (206) of cartridge body (202), lower portion (406) of each bristle cluster (402) extends beyond the plane (416) formed by the lower surfaces (420) of each nodule (412) and into elongate slot (206). In this first configuration, bristle clusters (402) are inserted into elongate slot (206) with a press fit to provide a secure yet releasable coupling between adjunct (400) and cartridge body (202). Each bristle cluster (402) is further configured to translate within each cavity (414) such that, in the second configuration where adjunct (400) is decoupled from elongate slot (206) of cartridge body (202), lower portion (406) of each bristle cluster (402) moves above the plane (416) formed by the lower surfaces (420) of each nodule (412) to thereby release adjunct (400) from staple cartridge (200). In this second configuration, upper portions (404) do not extend beyond the upper plane (418) defined by the upper surfaces (422) of nodules (412).

As shown in FIG. 15A, adjunct (400) may be selectively attached to staple cartridge deck (204) via bristle clusters (402) when bristle clusters (402) are in the extended state. As shown in FIG. 15B, adjunct (400) may be released from staple cartridge deck (204) by way of leading cam surface (217) of wedge sled (209) (see FIGS. 14A-14B) contacting lower surfaces (406) of bristle clusters (402) sequentially and driving them upwardly out of elongated slot (206). More particularly, bristle clusters (402) of the present version are configured to retract from elongated slot (206) and actively release adjunct (400) from staple cartridge deck (204) in response to firing of staple cartridge (200) during a staple firing by way of firing member (211) driving wedge sled (209), and also cutting edge (215), distally. Further, adjunct (400), including bristle clusters (402), may be split in half longitudinally (i.e., parallel to axis A2) during a firing stroke of surgical stapler (10) in a manner similar to that described above in connection with adjunct (330). In particular, cutting edge (215) is configured to cut through the bristles, or otherwise separate the bristles, of bristle clusters (402) in addition to cutting through a body of adjunct (400) and tissue during a firing stroke, therefore severing adjunct (400) approximately in half longitudinally during the firing stroke.

Figure 16A:
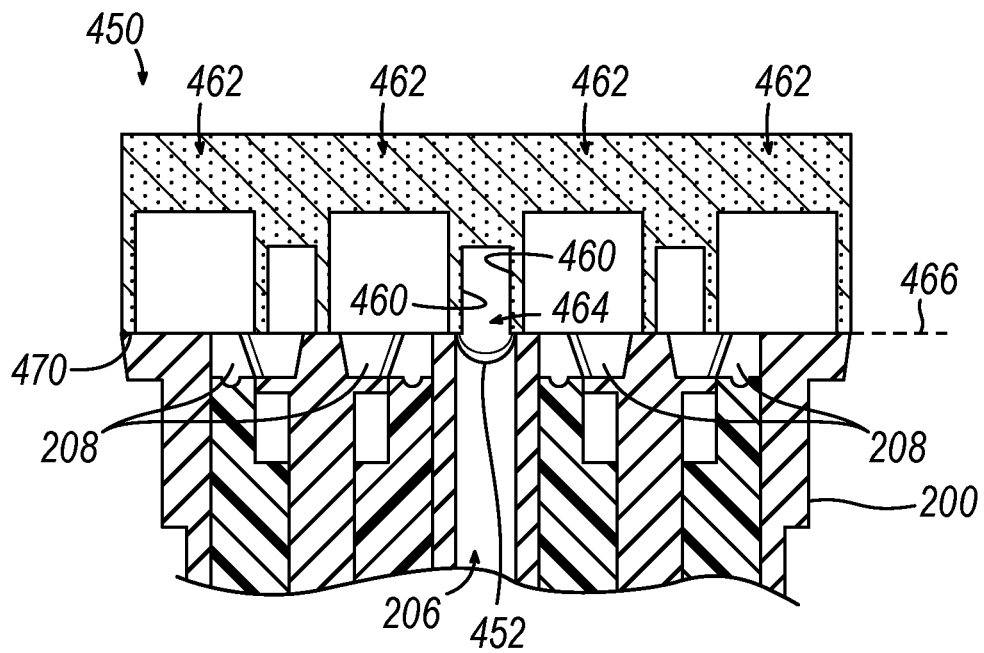
FIG. 16A depicts a cross-sectional view taken along a transverse axis of a fourth exemplary adjunct configured for use with the staple cartridge of FIG. 10, shown in an early stage of a firing stroke.
Figure 16B:
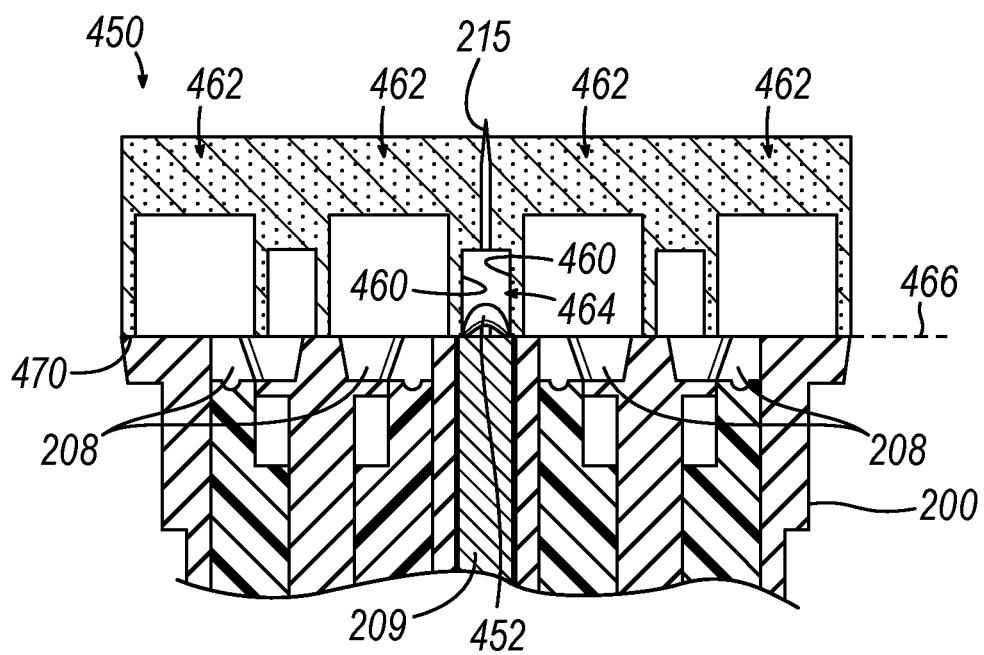
FIG. 16B depicts a cross-sectional view taken along the transverse axis of the adjunct of FIG. 16A, shown in a later stage of a firing stroke.

FIGS. 16A-16B show another exemplary compressible adjunct (450) configured for releasable attachment to staple cartridge (200). Adjunct (450) includes all of the same features as adjuncts (330, 400), except for the differences as noted below. Specifically, adjunct (450) provides an alternative to pins (340) and bristle clusters (402). In the example shown, adjunct (450) instead includes one or more attachment features in the form of bi-modal members (452) arranged along a longitudinal centerline of adjunct (450), with each bi-modal member (452) being positioned within a cavity (464) between adjacent side surfaces (460) of nodules (462) and configured to be at least partially received within elongate slot (206) of staple cartridge (200). Bi-modal members (452) may be comprised of, for example, fibrous materials or other materials exhibiting suitable strength and flexibility. Similar to adjuncts (330, 400), for adjunct (450), each bi-modal member (452) is configured to tightly fit within elongated slot (206) and move within its respective cavity (464) formed between adjacent side surfaces (460) separating distinct nodules (462).

Each bi-modal member (452) is configured to move within its respective cavity (464) such that, in the first configuration where adjunct (450) is coupled with elongate slot (206) of cartridge body (202), bi-modal member (452) extends beyond the plane (466) formed by the lower surfaces (470) of each nodule (462) and into elongate slot (206). In this first configuration, bi-modal members (452) are inserted into elongate slot (206) with a press fit to provide a secure yet releasable coupling between adjunct (450) and cartridge body (202). Each bi-modal member (452) is further configured to reconfigure, such as by inverting from a first bi-modal configuration to a second bi-modal configuration, within each cavity (464) such that, in the second configuration where adjunct (450) is decoupled from elongate slot (206) of cartridge body (202), bi-modal members (452) thereby release adjunct (450) from staple cartridge (200).

As shown in FIG. 16A, adjunct (450) may be selectively attached to staple cartridge deck (204) via bi-modal members (452) when bi-modal members (452) are in the outwardly extended state. As shown in FIG. 16B, adjunct (450) may be released from staple cartridge deck (204) by way of leading cam surface (217) of wedge sled (209) contacting bi-modal members (452) sequentially and inverting them upwardly out of elongated slot (206) and into the path of cutting edge (215) (see FIGS. 14A-14B). More particularly, bi-modal members (452) of the present version are configured to retract from elongated slot (206) and actively release adjunct (450) from staple cartridge deck (204) in response to firing of staple cartridge (200) during a staple firing by way of firing member (211) driving wedge sled (209), and also cutting edge (215), distally. Further, adjunct (450) may be split in half longitudinally (i.e., parallel to axis A2) during a firing stroke of surgical stapler (10) in a manner similar to that described above in connection with adjunct (330). Because each bi-modal member (452) is positioned within elongated slot (206), cutting edge (215) is configured to cut through bi-modal members (452) in addition to cutting through a body of adjunct (450) and tissue during a firing stroke, therefore severing adjunct (450) approximately in half longitudinally during the firing stroke.

While pins (340), bristle clusters (402), and bi-modal members (452) have been described as being incorporated into compressible monolithic adjuncts (330, 400, 450), it will be appreciated that bristle clusters (402) may just as easily be incorporated into a multi-layer adjunct similar to buttress assemblies (110, 112) described above in connection with FIGS. 7-9.

B. Exemplary Adjuncts with Staple Opening Attachment Features

Figure 17A:
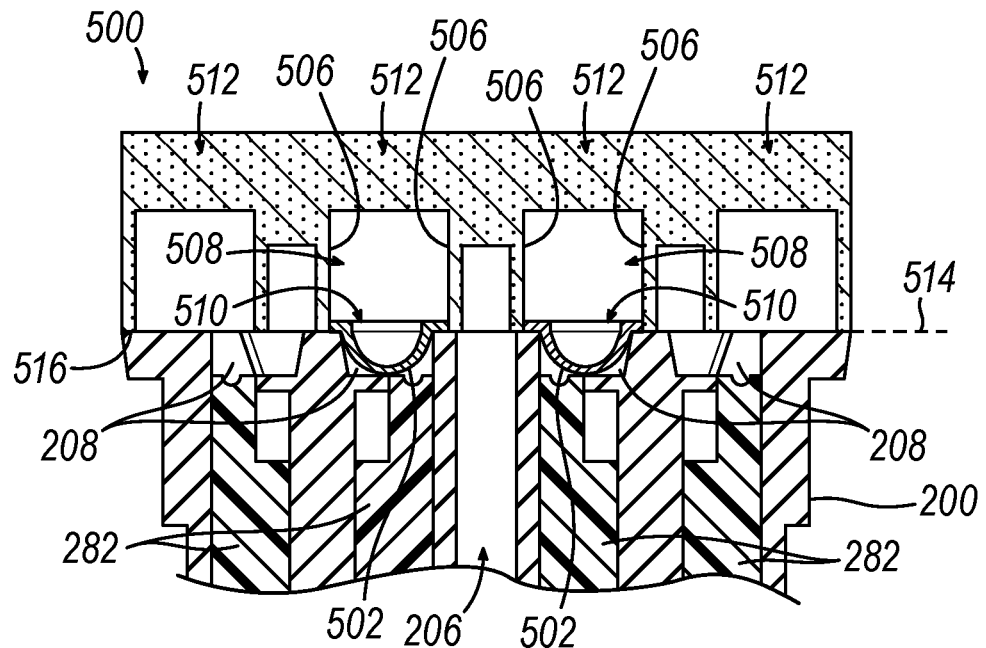
FIG. 17A depicts a cross-sectional view taken along a transverse axis of a fifth exemplary adjunct configured for use with the staple cartridge of FIG. 10, shown in an early stage of a firing stroke.
Figure 17B:
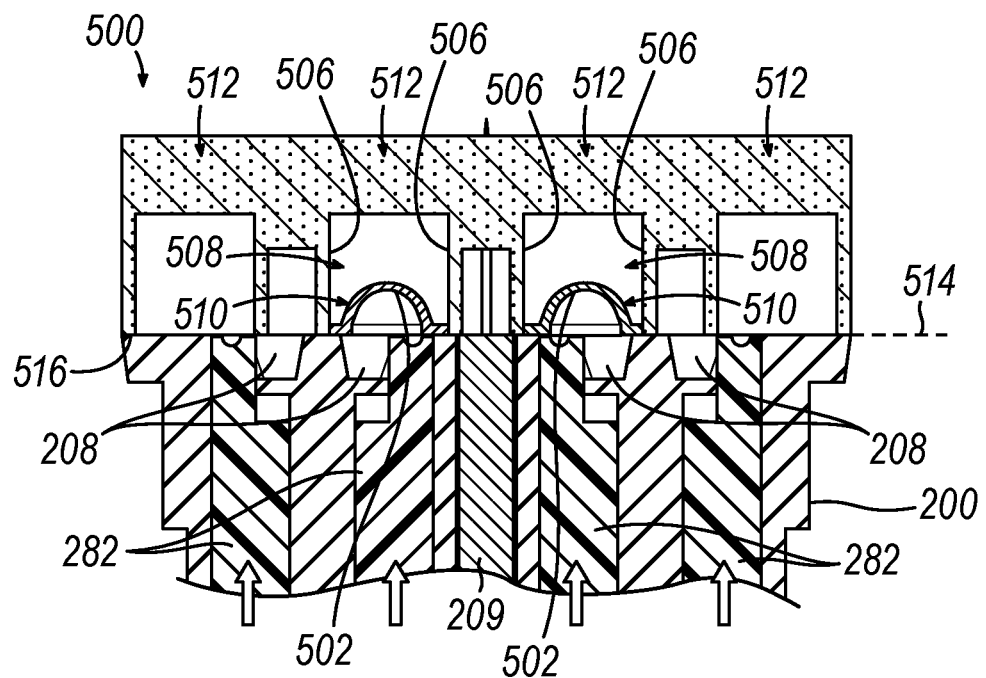
FIG. 17B depicts a cross-sectional view taken along the transverse axis of the adjunct of FIG. 17A, shown in a later stage of a firing stroke.

FIGS. 17A-17B show another exemplary compressible adjunct (500) configured for releasable attachment to staple cartridge (200). Adjunct (500) includes all of the same features as adjuncts (330, 400, 450), except for the differences as noted below. Specifically, adjunct (500) provides an alternative to pins (340), bristle clusters (402), and bi-modal members (452). In the example shown, adjunct (500) instead includes one or more attachment features in the form of bi-modal members (502). Bi-modal members (502) may be comprised of, for example, fibrous materials or other materials exhibiting suitable strength and malleability. Bi-modal members (502) are positioned at and are configured to transition into and out of openings (510) formed between adjacent inward facing surfaces (506) of nodules (512). Further, bi-modal members (502) are configured to be at least partially received within staple openings (208) of staple cartridge (200), rather than being configured to tightly fit within elongated slot (206). Each bi-modal member (502) of the present version is shown having a semi-spherical shape, though it will be appreciated that bi-modal members (502) may have various alternative shapes in other versions.

Each bi-modal member (502) is configured to move within each cavity (508) of a respective nodule (512) such that, in the first configuration where adjunct (500) is coupled with cartridge body (202), bi-modal members (502) extend beyond the plane (514) formed by the lower surfaces (516) of each nodule (512). In this first configuration, bi-modal members (502) are inserted into elongate staple openings (208) with a press fit to provide a secure yet releasable coupling between adjunct (500) and cartridge body (202). Each bi-modal member (502) is further configured to reconfigure, such as by inverting from a first bi-modal configuration to a second bi-modal configuration, within each cavity (508) such that, in the second configuration where adjunct (500) is decoupled from staple openings (208) of cartridge body (202), bi-modal members (502) thereby release adjunct (500) from staple cartridge (200). In some versions, bi-modal members (502) may be formed of a suitable material that promotes tissue in-growth into nodules (512) when bi-modal members (502) are in the inverted, second configuration following application of adjunct (500) to tissue via stapling.

As shown in FIG. 17A, adjunct (500) may be selectively attached to staple cartridge deck (204) via bi-modal members (502) when bi-modal members (502) are in the outwardly extended state. As shown in FIG. 17B, adjunct (500) may be released from staple cartridge deck (204) by way of wedge sled (209) driving staples (80) (see FIGS. 4-5B) through staple openings (208) such that at least one of staples (80) or staple driver (282) also contacts bi-modal members (502) sequentially and inverts them upwardly out of staple openings (208). More particularly, bi-modal members (502) of the present version are configured to retract from staple openings (208) and actively release adjunct (500) from staple cartridge deck (204) in response to firing of staple cartridge (200) during a staple firing by way of firing member (211) driving wedge sled (209), and also cutting edge (215), distally. Further, adjunct (500) may be split in half longitudinally (i.e., parallel to axis A2) during a firing stroke of surgical stapler (10) in a manner similar to that described above in connection with adjunct (330). In particular, cutting edge (215) is configured to cut through adjunct (500) in addition to cutting through tissue during a firing stroke, therefore severing adjunct (500) approximately in half longitudinally during the firing stroke.

Figure 18:
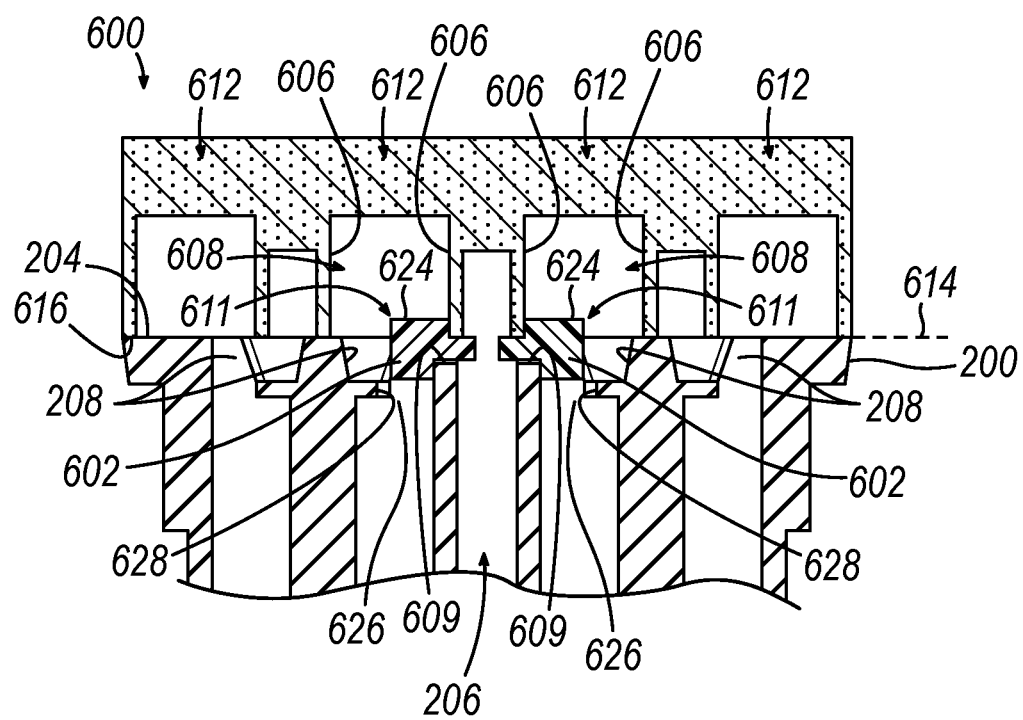
FIG. 18 depicts a cross-sectional view taken along a transverse axis of a sixth alternative exemplary adjunct configured for use with the staple cartridge of FIG. 10.
Figure 19:
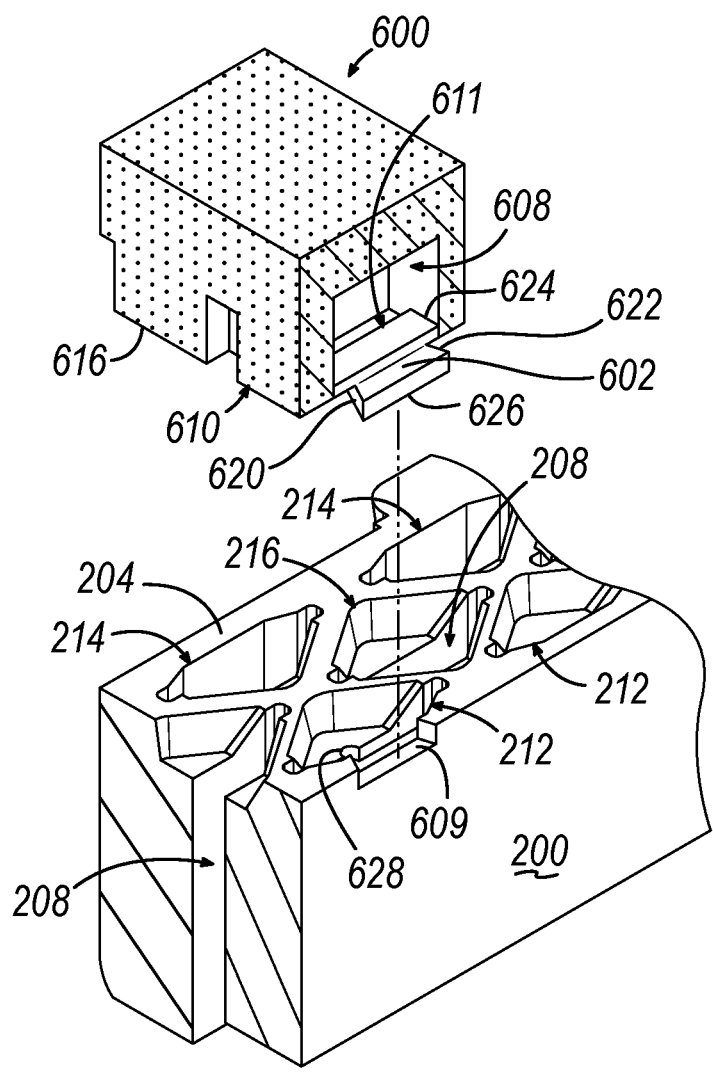
FIG. 19 depicts a cross-sectional perspective view of a portion of the adjunct of FIG. 18, shown separated from the staple cartridge.

FIGS. 18-19 show another exemplary compressible adjunct (600) configured for releasable attachment to staple cartridge (200). Adjunct (600) includes all of the same features as adjuncts (330, 400, 450, 500), except for the differences as noted below. Specifically, adjunct (600) provides an alternative to pins (340), bristle clusters (402), bi-modal members (452), and bi-modal members (502). In the example shown, adjunct (600) instead includes one or more attachment features in the form of protrusions (602). Protrusions (602) may be comprised of, for example, compressible materials or other materials exhibiting suitable strength and flexibility. Protrusions (602) may be generally trapezoidal in shape to interference fit within V-shaped notches (609) formed in staple cartridge deck (204) adjacent to staple openings (208), whereby protrusions (602) have two angular sides (620, 622) and a parallel top surface (624) and bottom surface (626), the top surface (624) having a larger surface area than the bottom surface (626) so as to fit within V-shaped notches (609). Protrusions (602) may be configured to transition into and out of openings (611) defined by V-shaped notches (609). In some versions, protrusions (602) may be configured to be at least partially received within staple openings (208) of staple cartridge (200), or a combination of being received within staple openings (208) and V-shaped notches (609), such as via press-fit or interference fit.

Each protrusion (602) is configured to move within each cavity (608) such that, in the first configuration where adjunct is coupled with cartridge body (202), protrusions (602) extend beyond the plane (614) formed by the lower surfaces (616) of each nodule (612). In this first configuration, protrusions (602) are inserted into V-shaped notches (609) with a press fit to provide a secure yet releasable coupling between adjunct (600) and cartridge body (202). Each protrusion (602) is further configured to reconfigure, such as by sliding in a direction toward adjunct (600) to a second configuration, within each cavity (608) such that, in the second configuration where adjunct (600) is decoupled from staple openings (208) of cartridge body (202), protrusions (602) thereby release adjunct (600) from staple cartridge (200).

As shown in FIG. 19, adjunct (600) may be selectively attached to staple cartridge deck (204) via protrusions (602) when protrusions (602) are in the outwardly extended state and thereby press-fit into V-shaped notches (609), whereby V-shaped notches (609) open laterally to respective staple openings (208). Adjunct (600) may be released from staple cartridge deck (204) by way of wedge sled (209) driving staples (80) vertically (parallel to the A1 axis) through staple openings (208) such that wedge sled (209) also contacts protrusions (602) and transitions them out of staple openings (208). More particularly, protrusions (602) of the present version are configured to retract from V-shaped notches (609) and actively release adjunct (600) from staple cartridge deck (204) in response to firing of staple cartridge (200) during a staple firing by way of firing member (211) driving wedge sled (209), and also cutting edge (215), distally. Further, adjunct (600) may be split in half longitudinally (i.e., along axis A2) during a firing stroke of surgical stapler (10). Similar to cutting edge (62), firing member (211) is configured to simultaneously cut tissue during a firing stroke via distally presented cutting edge (62). Also, cutting edge (215) is configured to cut through adjunct (600) in addition to cutting through tissue during a firing stroke, therefore severing adjunct (600) approximately in half longitudinally during the firing stroke. The V-shaped staple openings (208) are shaped to hold the material of adjunct (600) stationary to reduce the stretching or shearing of the material during cutting.

In some versions, a small hole (628) may be formed through the base surface of one or more recesses (212, 214, 216) such that hole (628) opens laterally to the corresponding staple opening (208). Holes (628) may be configured to align the staple drivers (see FIGS. 15A-18) axially within staple openings (208). Further, portions of adjunct (600) may be shaped to at least partially occupy holes (628).

C. Exemplary Adjunct with Lateral Release Features

Figure 20:
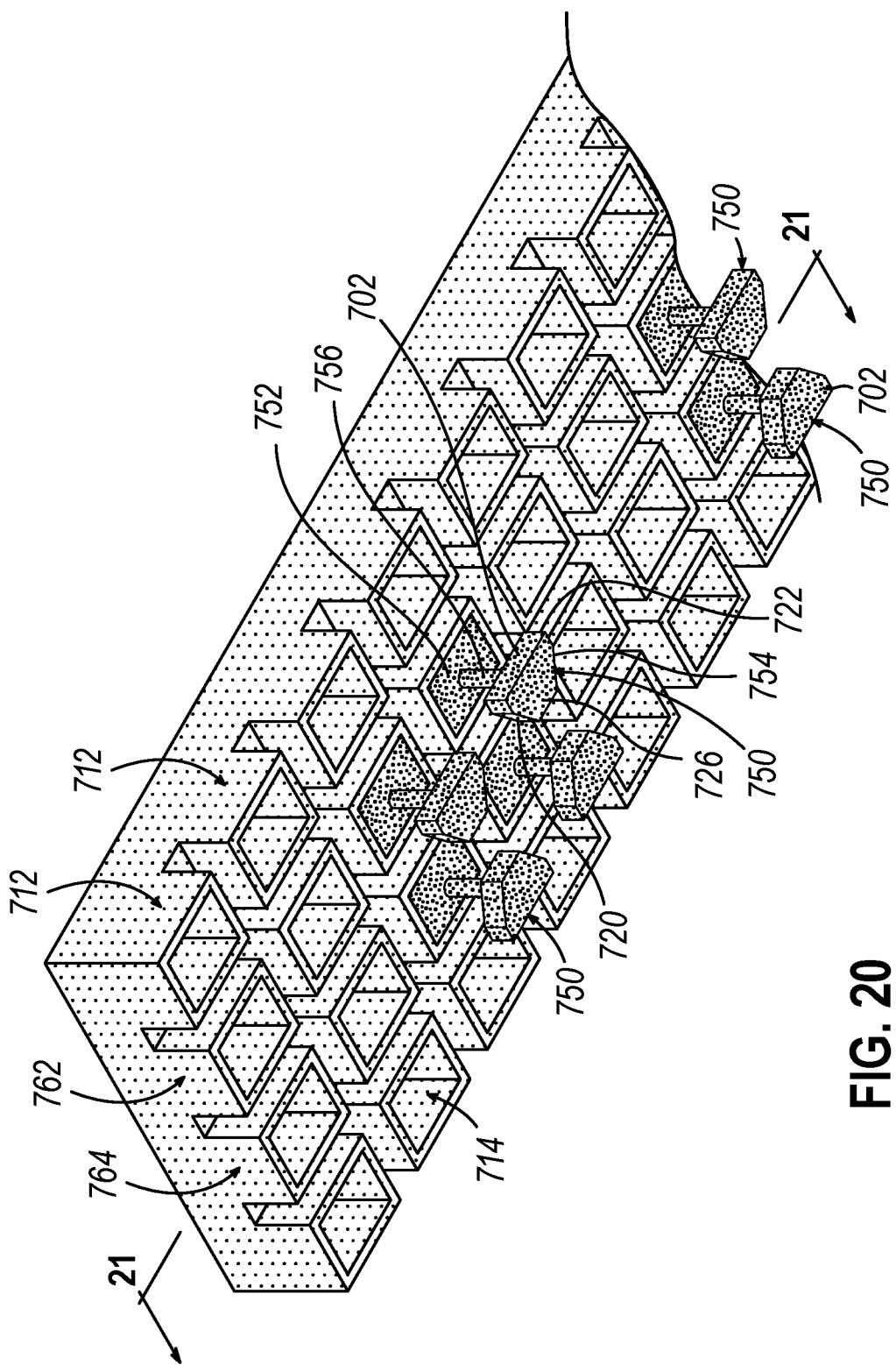
FIG. 20 depicts a perspective view of a seventh alternative exemplary adjunct configured for use with the staple cartridge of FIG. 10.
Figure 21:
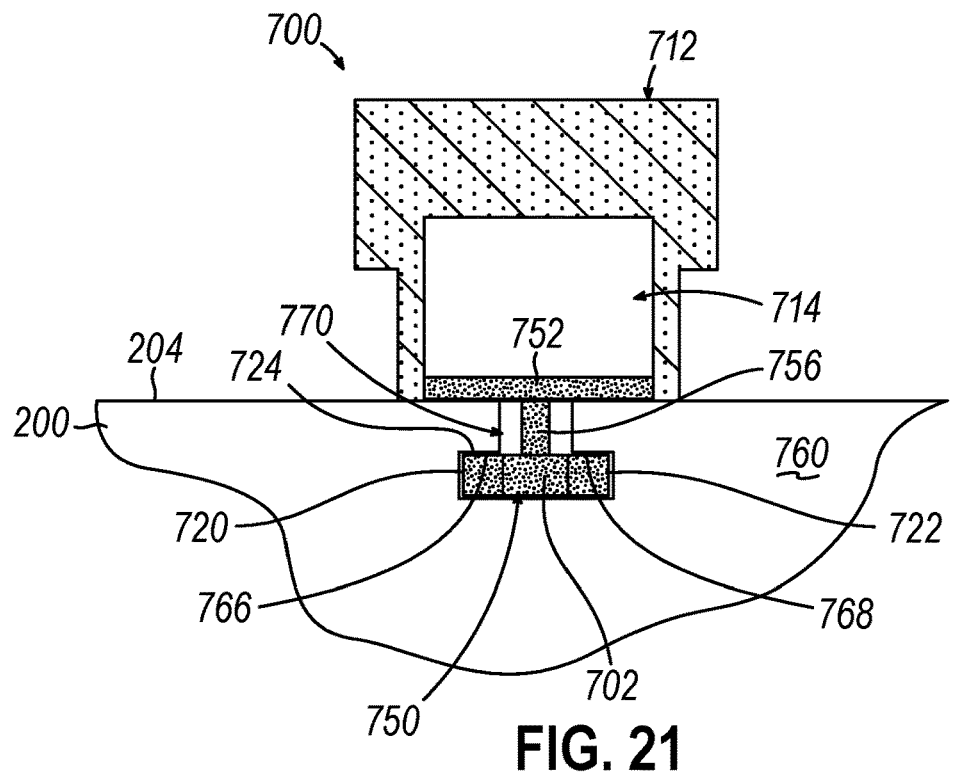
FIG. 21 depicts a cross-sectional view of the adjunct of FIG. 20, taken along line 21-21 of FIG. 20, shown coupled with the staple cartridge.
Figure 22:
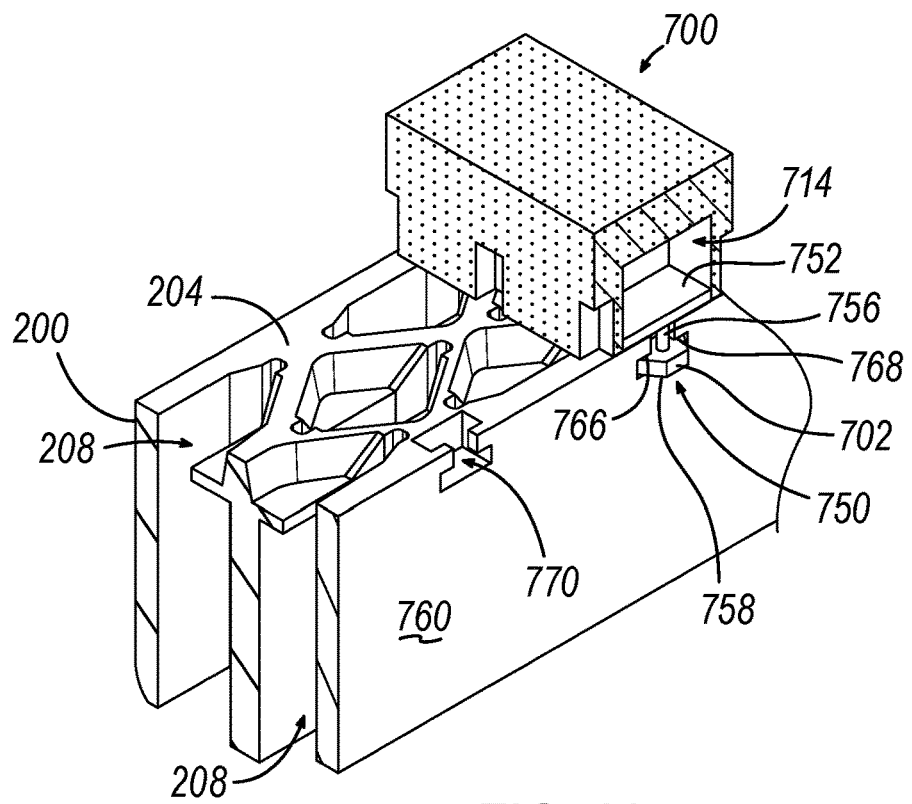
FIG. 22 depicts a cross-sectional perspective view of the adjunct of FIG. 20, taken along line 21-21 of FIG. 20, shown coupled with the staple cartridge.

FIGS. 20-22 show another exemplary compressible adjunct (700) configured for releasable attachment to staple cartridge (200). Adjunct (700) includes all of the same features as adjuncts (330, 400, 450, 500, 600), except for the differences as noted below. Specifically, adjunct (700) provides an alternative to pins (340), bristle clusters (402), bi-modal members (452), bi-modal members (502), and protrusions (602). In the example shown, adjunct (700) instead includes one or more attachment features in the form of protrusions (702). Protrusions (702) may be comprised of, for example, compressible materials or other materials exhibiting suitable strength and flexibility. Each protrusion (702) includes a lower portion (754) that may be generally trapezoidal in shape at a lower end (750) of protrusion (702), and an upper base portion (752) coupled with the lower trapezoidal portion (754) via a post (756). Trapezoidal portions (754) of protrusions (702) have two angular sides (720, 722) and a parallel top surface (724) and bottom surface (726), the top surface (724) having a larger surface area than the bottom surface (726).

In operation, trapezoidal portions (754) of protrusions (702) are configured to transition into and out of corresponding slots (770) (see FIG. 22) formed on the interior longitudinal surfaces (760) (see FIG. 22, only one such surface shown) defining elongate slot (206) of cartridge body (202). Further, base portions (752) are configured to be at least partially received within cavities (714) of nodules (712), such as via press-fit or interference fit, to hold them within nodules (712). As such, interior rows (762, 764) of nodules (712) aligned immediately adjacent to each side of elongate slot (206) may include one or more protrusions (702), while all other nodules (712) need not house any protrusions (702). It should be understood that in some versions, nodules (712) not including protrusions (702) may instead include other attachment features, for example, protrusions (602) as described above.

Trapezoidal portions (754) of protrusions (702) are configured to move laterally within each slot (770) in a direction transverse to a longitudinal axis of staple cartridge (200) defined by elongate slot (206) of cartridge body (202). In a first extended configuration, part of each trapezoidal portion (754) extends at least partially, laterally into elongate slot (206) on each side of elongate slot (206) to provide a secure yet releasable coupling between adjunct (700) and cartridge body (202). Each trapezoidal portion (754) is further configured to laterally transition, such as by bending or flexing of post (756), in a direction away from elongate slot (206) to a position within the respective slot (770), in response to firing of staple cartridge (200), such that protrusions (702) may retract upwardly into cavities (714) of nodules (712) into a second configuration and thereby allow adjunct (700) to release from staple cartridge (200).

As best shown in FIG. 22, adjunct (700) may be selectively attached to staple cartridge deck (204) via protrusions (702) when protrusions (702) are in the outwardly extended configuration and thereby extending at least partially laterally into elongate slot (206). In that configuration, adjunct (700) is coupled with staple cartridge (200) and held securely into place as upper surface (724) of trapezoidal portion (754) abuts against surfaces (766, 768) of slots (770) to prevent upward movement of adjunct (700) relative to staple cartridge deck (204).

Figure 23A:
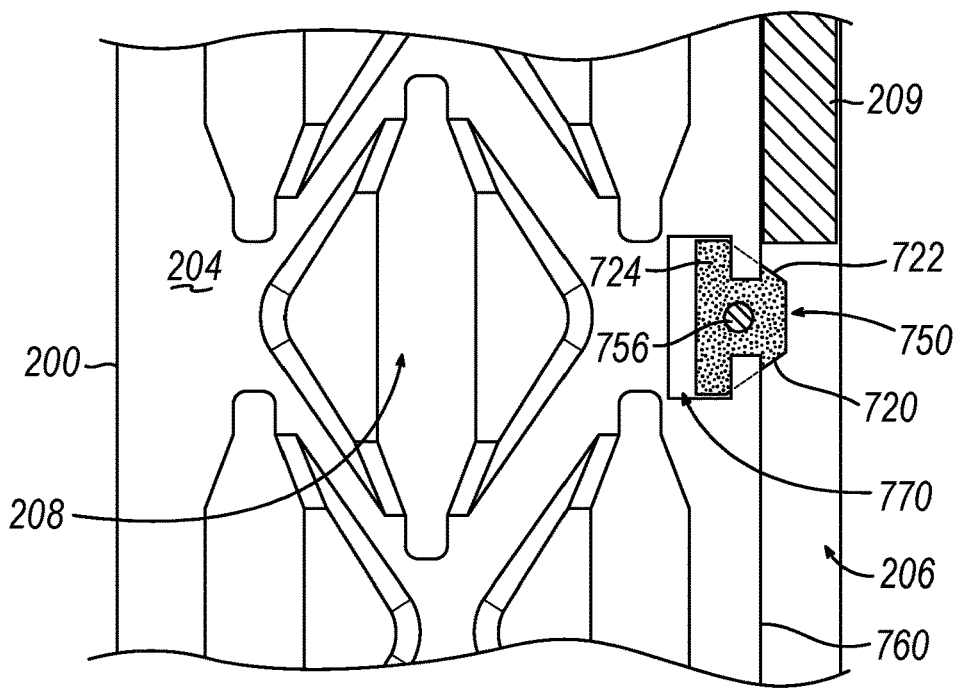
FIG. 23A is a top cross-sectional view of the adjunct of FIG. 20, shown coupled with the staple cartridge, and shown in an early stage of a firing stroke.
Figure 23B:
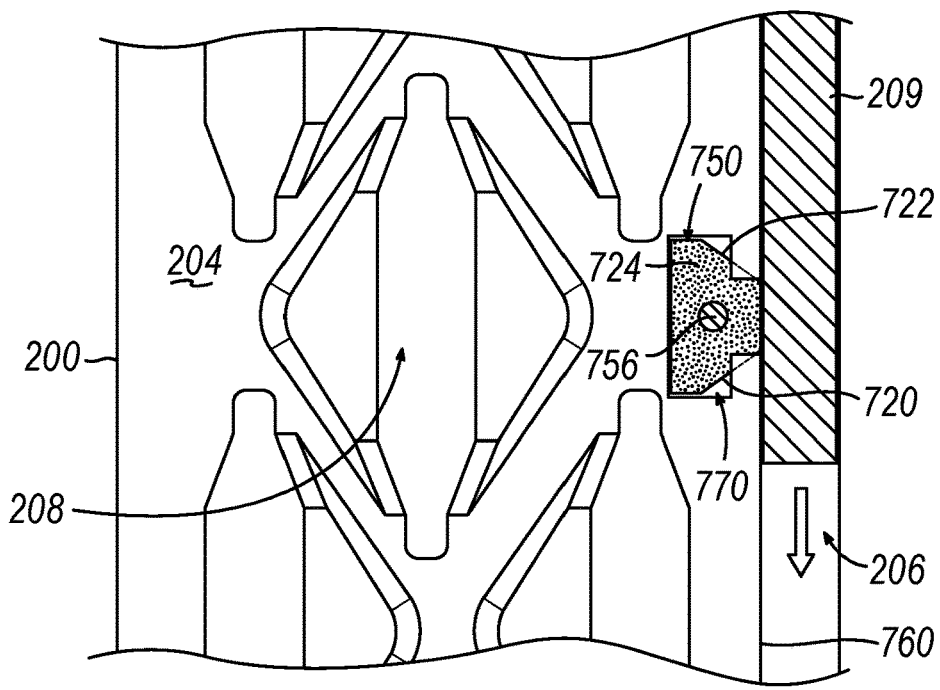
FIG. 23B is a top cross-sectional view of the adjunct of FIG. 20, shown coupled with the staple cartridge, and shown in a later stage of a firing stroke.

Shown in FIG. 23A is trapezoidal portion (754) of a protrusion (702) in the outwardly extended configuration and thereby extending at least partially into elongate slot (206) prior to firing of staple cartridge (200). As shown in FIG. 23B, adjunct (700) may be released from staple cartridge deck (204) by way of firing member (211) driving wedge sled (209), and also cutting edge (215), distally through elongate slot (206). Particularly, as firing member (211) and wedge sled (209) translate through elongate slot (206), they contact angled side (722) of trapezoidal portion (754) and move trapezoidal portion (754) into cavity (770) and out of elongate slot (206). Therefore, surfaces (766, 768) of slot (770) no longer prevent adjunct (700) from separating from staple cartridge deck (204), thus adjunct (700) may be released from staple cartridge deck (204).

It will be appreciated that shafts (756) of protrusions (702) in the first extended configuration may be stretched downwardly in tension while trapezoidal portions (754) are captured within cavities (770) of staple cartridge (200). When staple cartridge (200) is fired such that wedge sled (209) or firing member (211) drives trapezoidal portions (754) laterally outwardly from elongate slot (206), the tension of shafts (756) may resiliently retract trapezoidal portions (754) upwardly from cavities (770) and at least partially into nodule cavities (714) of adjunct (700), providing protrusions (702) in the second retracted configuration. In some versions, protrusions (702) may be configured such that in the second retracted configuration lower surfaces (726) of trapezoidal portions (702) are approximately flush with or recessed upwardly relative to the bottom surfaces of adjunct nodules (712). For instance, the upper base portion (752) of each protrusion (702) may itself be recessed upwardly within the respective nodule cavity (714), and/or upper base portion (752) may be configured to invert within nodule cavity (714) similar to bi-modal members (502) described above.

Further, adjunct (700) may be split in half longitudinally (i.e., parallel to axis A2) during a firing stroke of surgical stapler (10) in a manner similar to that described above in connection with adjunct (330). In particular, cutting edge (215) is configured to cut through adjunct (700) in addition to cutting through tissue during a firing stroke, therefore severing adjunct (700) approximately in half longitudinally during the firing stroke.

D. Exemplary Adjunct with Vertical Release Features

Figure 24:
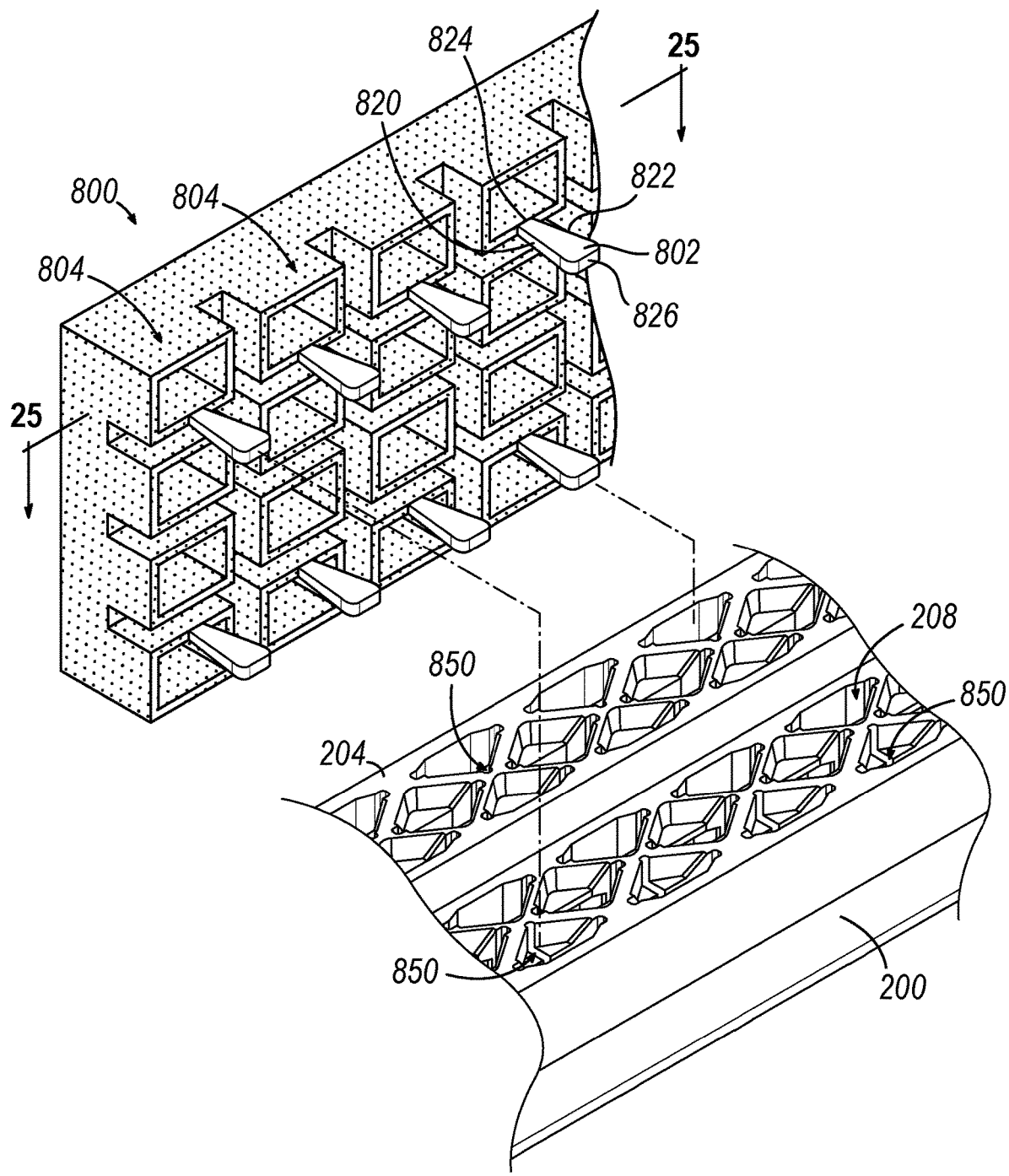
FIG. 24 depicts a perspective view of an eighth alternative exemplary adjunct configured for use with the staple cartridge of FIG. 10, shown separated from the staple cartridge and rotated 90-degrees.
Figure 25:
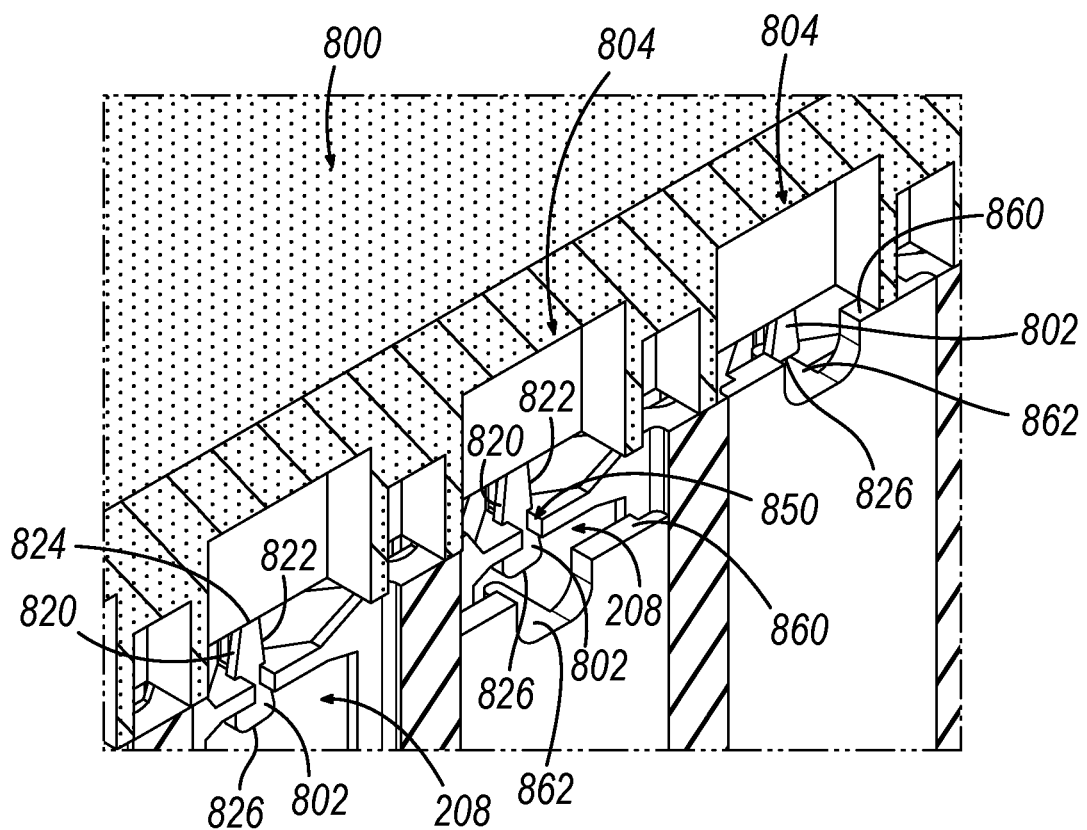
FIG. 25 depicts a cross-sectional perspective view of the adjunct of FIG. 24, taken along line 25-25 of FIG. 24, shown coupled with the staple cartridge.

FIGS. 24-25 show another exemplary compressible adjunct (800) configured for releasable attachment to staple cartridge (200). Adjunct (600) includes all of the same features as adjuncts (330, 400, 450, 500, 600, 700), except for the differences as noted below. Specifically, adjunct (800) provides an alternative to pins (340), bristle clusters (402), bi-modal members (452), bi-modal members (502), protrusions (602), and protrusions (702). In the example shown, adjunct (800) instead includes one or more attachment features in the form of tabs (802) that extend downwardly from nodules (804) of adjunct (800). Tabs (802) may be comprised of, for example, compressible foam materials or other materials exhibiting suitable strength and flexibility. Tabs (802) may be generally trapezoidal in shape to interference fit within staple openings (208), whereby tabs (802) have two angular sides (820, 822) and a parallel top surface (824) and bottom surface (826), the top surface (824) having a smaller surface area than the bottom surface (826). Tabs (802) are shaped to be at least partially received within slots (850) of staple cartridge deck (204) which are formed adjacent to staple openings (208), such that the larger bottom surface (826) is wider than the opening to slot (850).

Each tab (802) is configured to be inserted into a slot (850) in staple cartridge deck (204) with a press fit such that when adjunct (800) is attached with cartridge body (202), tabs (802) provide a secure yet releasable coupling between adjunct (800) and cartridge body (202). Each tab (802) is further configured to compress and transition out of slot (850) during a firing stroke such that adjunct (800) is decoupled from slots (850) of cartridge body (202), and tabs (802) thereby release adjunct (800) from staple cartridge (200).

As shown in FIG. 25, adjunct (800) may be selectively attached to staple cartridge deck (204) via tabs (802) when tabs (802) are inserted into slots (850). Adjunct (800) may be released from staple cartridge deck (204) by way of firing member (211) driving a wedge sled (209) distally to actuate modified staple drivers (860) positioned within staple openings (208) upwardly to thereby eject staples (not shown) from openings (208) and simultaneously push tabs (802) vertically (parallel to the A1 axis) out of slots (850) during a firing stroke. As shown in FIG. 25, each staple driver (860) includes an upper arm (862) configured to engage bottom surface (826) of the respective tab (802) and thereby drive tab (802) upwardly from its slot (850) during a firing stroke. Accordingly, tabs (802) of the present version are configured to retract from slots (850) and actively release adjunct (800) from staple cartridge deck (204) in response to firing of staple cartridge (200). Further, adjunct (800) may be split in half longitudinally (i.e., parallel to axis A2) during the firing stroke of surgical stapler (10) in a manner similar to that described above in connection with adjunct (330). In particular, cutting edge (215) is configured to cut through adjunct (800) in addition to cutting through tissue during a firing stroke, therefore severing adjunct (800) approximately in half longitudinally during the firing stroke.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) an adjunct body defining an adjunct surface for contacting a tissue, wherein the adjunct body is configured to overlie and directly contact a deck of a surgical stapler, wherein the surgical stapler includes a plurality of staples configured to affix the adjunct body to a tissue in response to a firing operation of the surgical stapler; and (b) a plurality of movable members coupled with the adjunct body, wherein each movable member of the plurality of movable members is individually operable to move from a first configuration to a second configuration in response to the firing operation of the surgical stapler; wherein the movable members in the first configuration are configured to couple the adjunct body with the deck, wherein the movable members in the second configuration are configured to enable the adjunct body to separate from the deck.

Example 2

The apparatus of Example 1, wherein the adjunct body defines an abutment surface shaped to contact the deck, wherein each of the plurality of movable members in the first configuration extends outwardly from the abutment surface.

Example 3

The apparatus of Example 2, wherein the adjunct body has a length defining a first axis and a thickness defining a second axis perpendicular to the first axis, wherein the staples of the surgical stapler are configured to advance parallel to the second axis during the firing operation, wherein each of the plurality of movable members is configured to translate parallel to the second axis to transition from the first configuration to the second configuration.

Example 4

The apparatus of any of Examples 1-3, wherein each movable member includes a pin.

Example 5

The apparatus of Example 4, wherein each pin is configured to be inserted into a slot defined by the deck with a press fit to couple the adjunct body to the deck.

Example 6

The apparatus of any of Examples 4-5, wherein the surgical stapler includes a cutting edge operable to translate along a slot of the deck extending between a proximal end of the deck and a distal end of the deck to cut the tissue, wherein each pin is configured to be cut by the cutting edge into two distinct portions during the firing operation.

Example 7

The apparatus of any of Examples 1-6, wherein each movable member includes a cluster of bristles.

Example 8

The apparatus of Example 7, wherein each cluster of bristles is configured to be inserted into a slot defined by the deck with a press fit to couple the adjunct body to the deck.

Example 9

The apparatus of any of Examples 7-8, wherein the surgical stapler includes a cutting edge operable to translate along a slot of the deck extending between a proximal end of the deck and a distal end of the deck to cut the tissue, wherein the cluster of bristles is configured to be separated by the cutting edge into two distinct portions during the firing operation.

Example 10

The apparatus of any of Examples 1-9, wherein each movable member includes a bi-modal feature, wherein each bi-modal feature in the first configuration is configured to be inserted into a slot defined by the deck with a press fit to couple the adjunct body to the deck.

Example 11

A surgical stapling assembly, comprising: (a) an end effector, including: (i) a first stapling surface including the deck, and (ii) a second stapling surface configured to cooperate with the first stapling surface to clamp and staple tissue; and (b) the apparatus of any of Examples 1-10 positioned on one of the first stapling surface or the second stapling surface.

Example 12

The apparatus of Example 11, wherein the surgical stapling assembly includes a cutting edge operable to translate along a slot of the deck extending between a proximal end of the deck and a distal end of the deck to cut the tissue, wherein each movable member in the first configuration extends into the slot.

Example 13

The apparatus of Example 12, wherein the slot defines a plurality of cavities each laterally aligned with at least one movable member, wherein each movable member is at least partially housed within the slot in the first configuration to couple the adjunct body to the deck, wherein each movable member is laterally transitioned out of the slot in the second configuration to assist the adjunct body to decouple from the deck.

Example 14

The apparatus of Example 11, wherein the deck includes a plurality of openings, wherein one or more staples are configured to pass through a corresponding opening of the plurality of openings during the firing operation.

Example 15

The apparatus of Example 14, wherein each of the movable members includes a bi-modal feature, wherein each bi-modal feature is configured to extend into at least one of the plurality of openings in the first configuration to couple the adjunct body to the deck, wherein each bi-modal feature is configured to retract from the at least one of the plurality of openings in the second configuration to assist the adjunct body to decouple from the deck.

Example 16

An apparatus, comprising: (a) an adjunct body defining an adjunct surface for contacting a tissue and an abutment surface configured to overlie and directly contact a deck of a stapling assembly of a surgical stapler, wherein the stapling assembly includes a plurality of staples configured to affix the adjunct body to a tissue in response to a firing operation of the surgical stapler; (b) one or more cavities formed on the abutment surface of the adjunct body; and (c) a plurality of movable members each housed within one of the one or more cavities, wherein each movable member of the plurality of movable members is individually operable to move from a first position to a second position relative to the adjunct body in response to the firing operation of the surgical stapler; wherein the movable members in the first position are configured to couple the adjunct body with the deck, wherein the movable members in the second position are configured to enable the adjunct body to separate from the deck.

Example 17

The apparatus of Example 16, wherein the surgical stapler includes a cutting edge operable to translate along a slot of the deck extending between a proximal end of the deck and a distal end of the deck to cut the tissue, wherein each movable member in a second position is configured to extend into the slot.

Example 18

The apparatus of Example 17, wherein each movable member is configured in the first position to press-fit into the slot to couple the adjunct body to the deck.

Example 19

The apparatus of any of Examples 16-18, wherein each of the movable members includes a bi-modal feature, wherein each bi-modal feature in the first position is configured to extend from one of the one or more cavities into the deck to couple the adjunct body to the deck.

Example 20

An apparatus for coupling with a surgical stapler, comprising: (a) an adjunct body defining an adjunct surface for contacting a tissue, wherein the adjunct body is configured to overlie and directly contact a deck of a stapling assembly of a surgical stapler; and (b) a plurality of attachment members each having a flexible post, wherein the flexible post of each of the plurality of attachment members is coupled with and extends from the adjunct body, wherein each flexible member of the plurality of attachment members is individually operable to transition from a first position to a second position in response to a firing operation of the surgical stapler to assist the adjunct body to decouple from the deck; wherein each attachment member is shaped such that in the first position the attachment member is configured to be positioned within a slot formed between a distal end and a proximal end of the surgical stapler to couple the adjunct body to the deck; and wherein the flexible post of each of the plurality of attachment members is configured to flex to laterally transition the attachment member out of the slot in the second position to assist the adjunct body to decouple from the deck.

VI. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. Pub. No. 2023/0139613, entitled "Discrete Adjunct Attachment Features for Surgical Stapler," published May 4, 2023, issued as U.S. Pat. No. 11,950,781 on May 4, 2024; and U.S. Pat. Pub. No. 2023/0140285, entitled "Compressible Adjunct for Surgical Stapler," published on May 4, 2023, issued as U.S. Pat. No. 11,998,204 on Jun. 4, 2024. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an adjunct body defining an adjunct surface configured to contact a tissue, wherein the adjunct body is configured to overlie and directly contact a deck of a surgical stapler, wherein the surgical stapler includes a plurality of staples configured to affix the adjunct body to a tissue in response to a firing operation of the surgical stapler; and
   (b) a plurality of movable members coupled with the adjunct body, wherein each movable member of the plurality of movable members includes a lower surface configured to contact a sled of the surgical stapler and be individually driven by the sled from a first configuration to a second configuration in response to the firing operation of the surgical stapler and sliding against the sled;
   wherein the movable members in the first configuration are configured to couple the adjunct body with the deck and are spaced apart from the adjunct surface such that a gap exists between the adjunct surface and the movable members,
   wherein the movable members in the second configuration are configured to enable the adjunct body to separate from the deck.

2. The apparatus of claim 1, wherein the adjunct body defines an abutment surface shaped to contact the deck, wherein each of the plurality of movable members in the first configuration extends outwardly from the abutment surface.

3. The apparatus of claim 2, wherein the adjunct body has a length defining a first axis and a thickness defining a second axis perpendicular to the first axis, wherein the staples of the surgical stapler are configured to advance parallel to the second axis during the firing operation, wherein each of the plurality of movable members is configured to translate parallel to the second axis to transition from the first configuration to the second configuration.

4. The apparatus of claim 1, wherein each movable member includes a pin.

5. The apparatus of claim 4, wherein each pin is configured to be inserted into a slot defined by the deck with a press fit to couple the adjunct body to the deck.

6. The apparatus of claim 4, wherein the surgical stapler includes a cutting edge operable to translate along a slot of the deck extending between a proximal end of the deck and a distal end of the deck to cut the tissue, wherein each pin is configured to be cut by the cutting edge into two distinct portions during the firing operation.

7. The apparatus of claim 1, wherein each movable member includes a cluster of bristles.

8. The apparatus of claim 7, wherein each cluster of bristles is configured to be inserted into a slot defined by the deck with a press fit to couple the adjunct body to the deck.

9. The apparatus of claim 7, wherein the surgical stapler includes a cutting edge operable to translate along a slot of the deck extending between a proximal end of the deck and a distal end of the deck to cut the tissue, wherein the cluster of bristles is configured to be separated by the cutting edge into two distinct portions during the firing operation.

10. The apparatus of claim 1, wherein each movable member includes a bi-modal feature, wherein each bi-modal feature in the first configuration is configured to be inserted into a slot defined by the deck with a press fit to couple the adjunct body to the deck.

11. A surgical stapling assembly, comprising:
    (a) an end effector, including:
       (i) a first stapling surface including the deck, and
       (ii) a second stapling surface configured to cooperate with the first stapling surface to clamp and staple tissue; and
    (b) the apparatus of claim 1 positioned on one of the first stapling surface or the second stapling surface.

12. The apparatus of claim 11, wherein the surgical stapling assembly includes a cutting edge operable to translate along a slot of the deck extending between a proximal end of the deck and a distal end of the deck to cut the tissue, wherein each movable member in the first configuration extends into the slot.

13. The apparatus of claim 12, wherein the slot defines a plurality of cavities each laterally aligned with at least one movable member, wherein each movable member is at least partially housed within the slot in the first configuration to couple the adjunct body to the deck, wherein each movable member is laterally transitioned out of the slot in the second configuration to assist the adjunct body to decouple from the deck.

14. The apparatus of claim 11, wherein the deck includes a plurality of openings, wherein one or more staples are configured to pass through a corresponding opening of the plurality of openings during the firing operation.

15. The apparatus of claim 14, wherein each of the movable members includes a bi-modal feature, wherein each bi-modal feature is configured to extend into at least one of the plurality of openings in the first configuration to couple the adjunct body to the deck, wherein each bi-modal feature is configured to retract from the at least one of the plurality of openings in the second configuration to assist the adjunct body to decouple from the deck.

16. An apparatus, comprising:
    (a) an adjunct body defining an adjunct surface configured to contact a tissue and an abutment surface configured to overlie and directly contact a deck of a stapling assembly of a surgical stapler, wherein the stapling assembly includes a plurality of staples configured to affix the adjunct body to a tissue in response to a firing operation of the surgical stapler, wherein the adjunct surface extends continuously along a lateral width of the adjunct body and along a longitudinal length of the adjunct body;
    (b) a plurality of cavities formed in the adjunct body, wherein two cavities of the plurality of cavities are aligned along the longitudinal length and are separated from each other by an opening in the abutment surface; and (c) a plurality of movable members each housed within a respective cavity of the plurality of cavities, wherein each movable member of the plurality of movable members is individually operable to linearly translate from a first position to a second position relative to the adjunct body in response to the firing operation of the surgical stapler;

wherein the movable members in the first position are configured to couple the adjunct body with the deck, wherein the movable members in the second position are configured to enable the adjunct body to separate from the deck and are positioned within the adjunct body.

17. The apparatus of claim 16, wherein the surgical stapler includes a cutting edge operable to translate along a slot of the deck extending between a proximal end of the deck and a distal end of the deck to cut the tissue, wherein each movable member in a first position is configured to extend into the slot.

18. The apparatus of claim 17, wherein each movable member is configured in the first position to press-fit into the slot to couple the adjunct body to the deck.

19. The apparatus of claim 16, wherein each of the movable members includes a bi-modal feature, wherein each bi-modal feature in the first position is configured to extend from one of the plurality of cavities into the deck to couple the adjunct body to the deck.

20. An apparatus for coupling with a surgical stapler, comprising:
(a) an adjunct body defining an adjunct surface configured to contact a tissue, wherein the adjunct body is configured to overlie and directly contact a deck of a stapling assembly of a surgical stapler; and
(b) a plurality of attachment protrusions each having a flexible post, wherein the flexible post of each of the plurality of attachment protrusions is coupled with and extends from the adjunct body, wherein each flexible post of the plurality of attachment protrusions is individually operable to transition from a first position to a second position in response to a firing operation of the surgical stapler to assist the adjunct body to decouple from the deck;

wherein each attachment protrusion is shaped such that in the first position the attachment protrusion is configured to be positioned within a slot formed between a distal end and a proximal end of the surgical stapler to couple the adjunct body to the deck; and wherein the flexible post of each of the plurality of attachment protrusions is configured to flex to thus laterally transition the attachment protrusion away from the slot in a direction transverse to a longitudinal axis of the surgical stapler and parallel to the deck such that the attachment protrusion transitions into the second position to assist the adjunct body to decouple from the deck.

* * * * *